United States Patent
Hamm-Alvarez et al.

(10) Patent No.: US 11,224,662 B2
(45) Date of Patent: Jan. 18, 2022

(54) METHODS AND THERAPEUTICS COMPRISING LIGAND-TARGETED ELPS

(71) Applicant: University of Southern California, Los Angeles, CA (US)

(72) Inventors: Sarah Hamm-Alvarez, Pasadena, CA (US); John Andrew MacKay, Pasadena, CA (US); Guoyong Sun, Mission Viejo, CA (US); Pang-Yu Hsueh, San Jose, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 16/230,698

(22) Filed: Dec. 21, 2018

(65) Prior Publication Data

US 2019/0375797 A1    Dec. 12, 2019

Related U.S. Application Data

(63) Continuation of application No. 14/811,720, filed on Jul. 28, 2015, now abandoned, which is a continuation of application No. 13/764,476, filed on Feb. 11, 2013, now abandoned.

(60) Provisional application No. 61/664,619, filed on Jun. 26, 2012, provisional application No. 61/598,298, filed on Feb. 13, 2012.

(51) Int. Cl.
| | |
|---|---|
| *A61K 47/64* | (2017.01) |
| *C07K 14/005* | (2006.01) |
| *C07K 16/28* | (2006.01) |
| *A61K 49/00* | (2006.01) |
| *A61K 38/00* | (2006.01) |
| *C07K 14/00* | (2006.01) |
| *C12N 7/00* | (2006.01) |

(52) U.S. Cl.
CPC ........ *A61K 47/6435* (2017.08); *C07K 14/005* (2013.01); *C07K 16/28* (2013.01); *A61K 38/00* (2013.01); *A61K 49/0043* (2013.01); *A61K 49/0056* (2013.01); *C07K 14/001* (2013.01); *C07K 16/283* (2013.01); *C07K 2319/33* (2013.01); *C07K 2319/74* (2013.01); *C12N 7/00* (2013.01); *C12N 2710/10033* (2013.01)

(58) Field of Classification Search
None
See application file for complete search history.

(56) References Cited

U.S. PATENT DOCUMENTS

| | | | |
|---|---|---|---|
| 4,898,926 A | 2/1990 | Urry | |
| 6,852,834 B2 | 2/2005 | Chilkoti | |
| 7,700,727 B2 | 4/2010 | Berthet et al. | |
| 7,829,681 B2 | 11/2010 | Seefeldt et al. | |
| 8,252,740 B2 | 8/2012 | Raucher et al. | |
| 8,367,626 B2 | 2/2013 | Furgeson et al. | |
| 8,513,380 B2 * | 8/2013 | Barker | A61P 17/02 530/300 |
| 8,563,521 B2 | 10/2013 | Skerra et al. | |
| 8,680,045 B2 | 3/2014 | Primiano et al. | |
| 8,841,137 B2 | 9/2014 | Delouise et al. | |
| 8,841,414 B1 | 9/2014 | Raucher et al. | |
| 8,933,197 B2 | 1/2015 | Stemmer et al. | |
| 9,102,763 B2 * | 8/2015 | MacKay | A61K 38/18 |
| 2002/0013344 A1 | 1/2002 | Steiner et al. | |
| 2007/0265197 A1 | 11/2007 | Furgeson et al. | |
| 2008/0312156 A1 | 12/2008 | Setton et al. | |
| 2010/0048473 A1 | 2/2010 | Chaikof et al. | |
| 2010/0104554 A1 | 4/2010 | Scott et al. | |
| 2010/0119529 A1 | 5/2010 | Furgeson et al. | |
| 2010/0189643 A1 | 7/2010 | Chilkoti et al. | |
| 2011/0039776 A1 | 2/2011 | Chilkoti | |
| 2011/0110866 A1 | 5/2011 | Chilkoti et al. | |
| 2011/0151006 A1 | 6/2011 | Weber et al. | |
| 2012/0213781 A1 | 8/2012 | Hilbert | |
| 2013/0196926 A1 | 8/2013 | MacKay et al. | |

(Continued)

FOREIGN PATENT DOCUMENTS

| | | |
|---|---|---|
| CN | 101544694 | 9/2009 |
| JP | 2006-182721 A | 7/2006 |

(Continued)

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*

(Continued)

*Primary Examiner* — Brian Gangle
*Assistant Examiner* — Andrea K McCollum
(74) *Attorney, Agent, or Firm* — Foley & Lardner LLP

(57) ABSTRACT

Disclosed herein are novel methods and compositions for targeting drug delivery systems to specific cells. One aspect relates to a drug delivery system comprising an elastin-like peptide (ELP) component and a ligand selected from the group consisting of an polymeric immunoglobulin receptor binding site in the Cα3 domain of dimeric human IgA (mIgA) and knob capable of either drug encapsulation or drug attachment. Further aspects relate to drug delivery systems comprising an elastin-like peptide (ELP) component and a ligand; wherein the ligand specifically binds to a receptor selected from the group consisting of coxsackievirus and adenovirus receptor (CAR) and polymeric immunoglobulin receptor (pIgR). Further aspects include the novel transcytosing properties of the elastin-like peptide and the ligand, knob. Also provided are methods and pharmaceutical compositions comprising the disclosed therapeutics.

17 Claims, 18 Drawing Sheets
Specification includes a Sequence Listing.

(56) References Cited

U.S. PATENT DOCUMENTS

| | | |
|---|---|---|
| 2013/0210747 A1 | 8/2013 | Hamm-Alvarez et al. |
| 2014/0294932 A1 | 10/2014 | Kim et al. |
| 2015/0209335 A1 | 7/2015 | MacKay et al. |
| 2015/0218280 A1 | 8/2015 | Epstein et al. |
| 2015/0238431 A1 | 8/2015 | Hamm-Alvarez et al. |
| 2016/0017004 A1 | 1/2016 | Hamm-Alvarez et al. |
| 2016/0168228 A1 | 6/2016 | Despanie |
| 2019/0022190 A1 | 1/2019 | Despanie et al. |
| 2019/0247317 A1 | 8/2019 | Hamm-Alvarez et al. |
| 2019/0282656 A1 | 9/2019 | MacKay et al. |
| 2019/0290726 A1 | 9/2019 | MacKay et al. |
| 2020/0062825 A1 | 2/2020 | Despanie et al. |
| 2020/0079868 A1 | 3/2020 | Epstein et al. |

FOREIGN PATENT DOCUMENTS

| | | | |
|---|---|---|---|
| WO | WO-95/33052 A1 | 12/1995 | |
| WO | WO-96/32406 | 10/1996 | |
| WO | WO-2008/033847 | 3/2008 | |
| WO | WO-2010/144612 | 12/2010 | |
| WO | WO-2011/006069 A1 | 1/2011 | |
| WO | WO-2011006069 A1 * | 1/2011 | ............ A61P 17/02 |
| WO | WO-2013/016578 A2 | 1/2013 | |
| WO | WO-2014/059384 | 4/2014 | |
| WO | WO-2014/059385 A1 | 4/2014 | |
| WO | WO-2014/161004 | 10/2014 | |
| WO | WO-2017/020686 A1 | 2/2017 | |

OTHER PUBLICATIONS

Chilkoti et al., "Stimulus responsive elastin biopolymers: applications in medicine and biotechnology", Current Opinion in Chemical Biology, vol. 10, No. 6, Dec. 1, 2006, pp. 652-657.

Database Geneseq [Online] Jun. 19, 2014 (Jun. 19, 2014), "ELP component reference polypeptide construct S48I48, SEQ ID 4 #1.", retrieved from EBI accession No. GSP:BBF47655 Database accession No. BBF47655, 1 page.

Despanie et al. "Elastin-like polypeptides: Therapeutic applications for an emerging class of nanomedicines," J Control Release, vol. 240, Nov. 11, 2015, pp. 93-108.

Final Office Action on U.S. Appl. No. 14/683,033 dated Dec. 6, 2019, 7 pages.

Floss et al., "Expression and Immunogenicity of the Mycobacterial Ag85B/ESAT-6 Antigens Produced in Transgenic Plants by Elastin-Like Peptide Fusion Strategy", Journal of Biomedicine and Biotechnology, vol. 2010, Jan. 1, 2010, pp. 1-14.

Hassouneh et al., "Fusions of elastin-like polypeptides to pharmaceutical proteins", Methods in Enzymology, vol. 502, 2012, pp. 215-237, NIH Public Access Author Manuscript Version internal pp. 1-24.

International Search Report and Written Opinion (ISA/US) for PCT Application No. PCT/US2017/035993, dated Aug. 16, 2017, 12 pages.

Janib et al., "Kinetic quantification of protein polymer nanoparticles using non-invasive imaging," Integr. Biol., vol. 5, No. 1, Jan. 2013, pp. 1-23.

NCBI, GenBank accession No. AAB59408.1 (Aug. 10, 2004), 1 page.

NCBI, GenBank accession No. NM_000558.3 (May 24, 2014), 7 pages.

Non-final Office Action on U.S. Appl. No. 14/965,053 dated Jun. 1, 2018, 23 pages.

Non-Final Office Action on U.S. Appl. No. 16/038,051 dated Dec. 31, 2019, 22 pages.

Non-Final Office Action on U.S. Appl. No. 16/125,538 dated Dec. 2, 2019, 22 pages.

Palmer et al., "Blood Substitutes", Annual Review of Biomedical Engineering, vol. 16, No. 1, Jul. 11, 2014, pp. 77-101.

Sheth et al., "Purification of monoclonal antibodies by affinity precipitation using thermally responsive elastin-like polypeptides(ELPs) fused to IgG binding domains: High-throughput analysis and scale up considerations.," Mar. 27, 2012, 1 page.

UnitProt Accession No. P68871, accessed May 28, 2018 at URL .unitprot.org/unitprot/ P68871, 25 pages.

UnitProt Accession No. P69891, accessed May 28, 2018 at URL .unitprot.org/unitprot/ P69891, 5 pages.

UnitProt Accession No. P69905, accessed May 28, 2018 at URL .unitprot.org/unitprot/ P69905, 21 pages.

Yampolsky et al., "The Exchangeability of Amino Acids in Proteins," Genetics, vol. 170, Aug. 2005, pp. 1459-1472.

Yeo et al., "Fabricated Elastin", Advanced Healthcare Materials, vol. 4, No. 16, Nov. 1, 2015, pp. 2530-2556.

Awasthi et al., "Biodistribution of Radioiodinated Adenovirus Fiber Protein Knob Domain after Intravenous Injection in Mice." J. Virol. 78(12):6431-6438 (2004).

Bork, Peer, "Powers and Pitfalls in Sequence Analysis: The 70% Hurdle", Genome Research, 2000, 10: pp. 398-400.

Bowie, et al., "Deciphering the Message in Protein Sequences: Tolerance to Amino Acid Substitutions", Science, vol. 247, No. 4948 (Mar. 16, 1990). pp. 1306-1310.

Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, vol. 111, Nov. 1990, pp. 2129-2138.

Chen, et al., "Enhancement and destruction of antibody function by somatic mutation: unequal occurrence is controlled by V gene combinatorial associations", The EMBO Journal, vol. 14, No. 12, pp. 2784-2794, 1995.

Chilkoti et al., "Design of thermally responsive, recombinant polypeptide carriers for targeted drug delivery." Advanced Drug Delivery Reviews 54(8):1093-1111 (2002).

Dhandhukia et al., "Switchable elaslin-like polypeptides that respond to chemical inducers of dimerization." Biomacromolecules Apr. 8, 2013, 14(4):976-85.

Dijoseph, et al., "CD20-Specific Antibody-Targeted Chemotherapy of Non-Hodgkins B-Cell Lymphoma Using Calicheamicin-Conjugated Rituximab." Cancer Immunol. Immunother, 56(7), pp. 1107-1117 (2007).

Dreher et al., "Temperature Triggered Self-Assembly of Polypeptides into Multivalent Spherical Micelles." J Am Chem Soc 130(2):687-694 (2008).

Fegan et al., "Chemically controlled protein assembly: techniques and applications." Chem Rev. 2010, 110(6):3315-36.

Final Office Action dated Jul. 23, 2018, from U.S. Appl. No. 14/420,308.

Final Office Action dated Jun. 28, 2018, from U.S. Appl. No. 14/811,720.

Floss, et al., "Elastin-Like Polypeptides Revolutionize Recombinant Protein Expression and their Biomedical Application." Trends in Biotechnology, vol. 28, No. 1, 37-45 (2009).

Floss, et al., "Influence of Elastin-Like Peptide Fusions on the Quantity and Quality of a Tobacco-Derived Human Immunodeficiency Virus-Neutralizing Antibody", Plant Biotechnology Journal 7, pp. 899-913 (2009).

Guo et al., "Anti-CD20 Tetravalent Antibody and Preparation Method and Application Thereof"., Google.com/patents pp. 1-19 (2009).

Hamm-Alvarez, "Design And Cellular Internalization Of Genetically Engineered Polypeptide Nanoparticles Displaying Adenovirus Knob Domain." Utah Drug Delivery Conference, 15th International Symposium on Recent Advances in Drug Delivery Systems "Drug Delivery: New Directions In A New Decade". Salt Lake City, Utah (Feb. 13-16, 2011).

Hassouneh, et al., "Fusions of Elastin-Like Polypeptides to Pharmaceutical Proteins", Methods of Enzymology, vol. 502, pp. 215-237 (2012).

Holliger P et al. (2005), "Engineered antibody fragments and the rise of single domains", Nature Biotechnology, vol. 23, No. 9, pp. 1126-1136.

Hsueh et al., "Development Of Novel Peptide Nanoparticles Targeted To Coxsackievirus-Adenovirus Receptor Expressing Cells." AAPS 2011, Washington, DC (Oct. 23-27, 2011).

(56) References Cited

OTHER PUBLICATIONS

Jubala, et al., "CD20 Expression in Normal Canine B Cells and in Canine non-Hodgkin Lymphoma", Vet Pathol 24, pp. 468-476, 2005.
Lazar, et al., "Transforming Growth Factor α: Mutation of Aspartic Acid 47 and Leucine 48 Results in Different Biological Activities", Molecular and Cellular Biology, Mar. 1988, vol. 8, No. 3, pp. 1247-1252.
MacEwan et al., "Elastin-like polypeptides: biomedical applications of tunable biopolymers." Biopolymers 94(1):60-77 (2010).
MacKay et al., "Ocular Drug Delivery Using A Thermo-responsive Lacritin Fusion Protein," Abstract of presentation at ARVO 2012, Fort Lauderdale, FL (May 4-6, 2012).
MacKay, "Genetically Engineered Polypeptide Nanoparticles." ACS Western Regional Meeting 2011, Pasadena, CA (Nov. 11, 2011).
MacKay, "Protein polymers—a platform for biopharmaceutical delivery and self-assembly." Keck Seminar (posted online Jun. 27, 2011).
McDaniel et al., "Drug delivery to solid tumors by elastin-like polypeptides." Adv Drug Deliv Rev. 2010, 62(15):1456-67.
McDaniel et al., "Recursive Directional Ligation by Plasmid Reconstruction Allows Rapid and Seamless Cloning of Oligomeric Genes." Biomacromolecules 11(4):944-952 (2010).
Meyer et al., "Purification of recombinant proteins by fusion with thermally-responsive polypeptides." Nature Biotechnology 17(11):1112-1115 (1999).
Non-Final Office Action dated Apr. 26, 2019, from U.S. Appl. No. 14/683,033.
Putnam et al., "Primary structure of a human IgA1 immunoglobulin. IV. Streptococcal IgA1 protease, digestion, Fab and Fc fragments, and the complete amino acid sequence of the alpha 1 heavy chain." J. Biol. Chem. 254:2865-2874 (1979).
Rudikoff, et al., "Single amino acid substitution altering antigen-binding specificity", Proc. Natl. Acad. Sci. USA, vol. 27 pp. 1979-1983, 1982.
Scheller, et al., "Forcing Single-Chain Variable Fragment Production in Tobacco Seeds by Fusion to Elastin-like Polypeptides". Plant Biotech. Journ, pp. 243-249, (2006).
Scheller, et al., "Purification of Spider Silk-Elastin from Transgenic Plants and Application for Human Chondrocyte Proliferation." Transgenic Research 13, pp. 51-57 (2004).
Shah et al., "Biodegradation of elastin-like polypeptide nanoparticles." Protein Sci. Epub May 14, 2012, 21(6):743-50.
Shi et al., "Elastin-based protein polymer nanoparticles carrying drug at both corona and core suppress tumor growth in vivo." J Control Release Epub May 25, 2013, 171(3):330-8.
Sun et al. "Design and cellular internalization of genetically engineered polypeptide nanoparticles displaying adenovirus knob domain" J Control Release. Oct. 30, 2011; 155(2):218-26. (Epub Jun. 14, 2011).
Sun et al., "Genetically engineered polypeptide nanoparticles targeted to lacrimal gland acinar cells." Presented at ARVO 2011, Fort Lauderdale, FL (May 1-5, 2011).
Supplement for Sun et al. "Design and cellular internalization of genetically engineered polypeptide nanoparticles displaying adenovirus knob domain" J Control Release. Oct. 30, 2011; 155(2):218-26. (Epub Jun. 14, 2011).
Trabbic-Carlson et al., "Expression and purification of recombinant proteins from *Escherichia coli*: Comparison of an elastin-like polypeptide fusion with an oligohistidine fusion." Protein Sci 13(12):3274-3284 (2004).
U.S. Final Office Action dated Mar. 9, 2017, for U.S. Appl. No. 14/684,162.
U.S. Office Action dated Jan. 4, 2018, from U.S. Appl. No. 14/683,033.
U.S. Office Action dated Mar. 31, 2017, from U.S. Appl. No. 14/420,308.
U.S. Office Action dated Mar. 9, 2018, from U.S. Appl. No. 14/684,162.
U.S. Office Action dated May 22, 2018, from U.S. Appl. No. 14/683,033.
UniProtKB/Swiss-Prot Direct Submission P62937.2. Locus PPIA_HUMAN. Oct. 3, 2012.[Retrieved from the Internet Jan. 17, 2014: <http://www.ncbi.nlm.nih.gov/protein/51702775?sat=16&satkey=10893480>].
U.S. Final Office Action for U.S. Appl. No. 13/764,476 dated Jun. 30, 2014, 15 pages.
U.S. Non-Final Office Action for U.S. Appl. No. 13/764,476 dated Nov. 1, 2013, 17 pages.
U.S. Non-Final Office Action for U.S. Appl. No. 14/684,162 dated Aug. 5, 2016, 16 pages.
U.S. Office Action dated Oct. 4, 2017, from U.S. Appl. No. 14/811,720.
U.S. Restriction Requirement for U.S. Appl. No. 13/764,476 dated Jun. 27, 2013, 10 pages.
U.S. Restriction Requirement for U.S. Appl. No. 14/420,308 dated Aug. 30, 2016, 8 pages.
U.S. Restriction Requirement for U.S. Appl. No. 14/684,162 dated Dec. 2, 2015, 11 pages.
Vignot et al., "mTOR-targeted therapy of cancer with rapamycin derivatives." Ann Oncol. 2005, 16(4):525-37.
Wang et al., "Control Of Ocular Drug Bioavailability Using Thermal-Responsive Polypeptides." Controlled Release Meeting (Aug. 3, 2011).
Welply et al. (1996), "A peptide isolated by phage display binds to ICAM-1 and inhibits binding to LFA-1", Proteins: Structure, Function, and Genetics, 26:262-270.
Wu et al., "Fabrication of elastin-like polypeptide nanoparticles for drug delivery by electrospraying," Biomacromolecules 2009, 10(1):19-24.
Wu, et al., "Humanization of a Murine Monoclonal Antibody by Simultaneous Optimization of Framework and CDR Residues", J. Mol. Biol., vol. 194, pp. 151-162, 1999.
Xie et al., "Novel Fiber-Dependent Entry Mechanism for Adenovirus Serotype 5 in Lacrimal Acini." J. Virol. 80(23):11833-11851 (2006).
Conference Program for the Division of Biochemical Technology (BIOT) of the American Chemical Society (ACS)National Meeting, pp. 18-193. San Diego, Mar. 25-29, 2012, Retrieved from the Internet on Feb. 23, 2014: http://www.che.udel.edu/mranton/pdf/acsbiot2012_conf.pdf, Mar. 4, 2012 (according to document properties for posted document).
Dreher et al. Temperature triggered self-assembly of polypeptides into multivalent spherical micelles. J Am Chem Soc. Jan. 16, 2008;130(2):687-94. doi: 10.1021/ja0764862. Epub Dec. 18, 2007.
Hamm-Alvarez, "Design And Cellular Internalization Of Genetically Engineered Polypeptide Nanoparticles Displaying Adenovirus Knob Domain." presented in Utah on Feb. 14, 2011, 34 pages.
Joensuu et al., "Expression and purification of an anti-Foot-and-mouth disease virus single-chain variable antibody fragment in tobacco plants", Transgenic Res., vol. 18, Apr. 3, 2009, pp. 685-696.
Meier and Greber. Adenovirus endocytosis. J Gene Med. Feb. 2004;6 Suppl 1 :S152-63. doi: 10.1002/jgm.553.
Rojas. Immunoglobulin transport across polarized epithelial cells. Nat Rev Mol Cell Biol. 2002;3(12):944-955. doi:10.1038/nrm972. Published: Dec. 1, 2002.
Urry. Physical Chemistry of Biological Free Energy Transduction As Demonstrated by Elastic Protein-Based Polymers. J. Phys. Chem. B 1997, 101, 51, 11007-11028. Publication Date:Dec. 18, 1997.
Wang et al., "Control Of Ocular Drug Bioavailability Using Thermal-Responsive Polypeptides." Controlled Release Meeting, Aug. 3, 2011, 1 page.
White KD and Capra JD. Targeting mucosal sites by polymeric immunoglobulin receptor-directed peptides. J Exp Med. 2002;196(4):551-555. doi:10.1084/jem.20020581. Aug. 19, 2002.
Xie et al. Novel fiber-dependent entry mechanism for adenovirus serotype 5 in lacrimal acini.J Virol. Dec. 2006;80(23):11833-51. doi: 10.1128/JVI.00857-06. Epub Sep. 20, 2006.

\* cited by examiner

L: acinar lumena
N: nucleus
APM: apical membrane
BM: basal-lateral membrane
CJ: cell junction

METHODS AND THERAPEUTICS COMPRISING LIGAND-TARGETED ELPS

CROSS-REFERENCE TO RELATED APPLICATIONS

This application is a continuation of U.S. application Ser. No. 14/811,720, filed Jul. 28, 2015, which is a continuation of U.S. application Ser. No. 13/764,476, filed Feb. 11, 2013, which claims the benefit under 35 U.S.C. § 119(e) to U.S. Provisional Application No. 61/598,298, filed Feb. 13, 2012, and U.S. Provisional Application No. 61/664,619, filed Jun. 26, 2012, the content of each of which is hereby incorporated by reference in its entirety.

STATEMENT OF GOVERNMENT SUPPORT

The presently disclosed subject matter was made with United States Government support under Grant Nos. EY017293-S1, EY017293 and 5-P30-CA14089, awarded by the National Institutes of Health (NIH). The United States Government has certain rights in the presently disclosed subject matter.

SEQUENCE LISTING

The instant application contains a Sequence Listing which has been submitted electronically in ASCII format and is hereby incorporated by reference in its entirety. Said ASCII copy, created on Aug. 21, 2019, is named 064189-5405_SL.txt and is 35,634 bytes in size.

BACKGROUND

Drug delivery to the eye (e.g. to retina, choroid, vitreous and optic nerve) is important for treating several disorders such as age-related macular degeneration, diabetic retinopathy, retinal venous occlusions, retinal arterial occlusion, macular edema, postoperative inflammation, infection, dryness, uveitis retinitis, proliferative vitreoretinopathy and glaucoma. Due to anatomic membrane barriers (i.e. cornea, conjunctiva and sclera) and the lacrimal drainage it can be quite challenging to target drugs and achieve therapeutic drug concentrations in the anterior parts of the eye after topical drug administration. Reaching the posterior part of the eye is an even more challenging task because of the anatomical and physiological barriers segregating this part of the eye from the anterior segment. Since those barriers cannot be altered with noninvasive methods, there is a need in the art for improved methods and pharmaceutical compositions that increase ocular bioavailability.

There is a need in the art for improved noninvasive, safe and patient-friendly drug delivery systems that are specific and effective for targeted delivery to the eye. In general, drugs can enter the eye via three distinctive routes, i.e. a) through conjunctiva/sclera after topical application, b) from the anterior part after topical application, and c) from the systemic circulation after topical application, parenteral, oral, and intranasal or other administration routes that deliver drugs to the blood circulation. Then drugs can be delivered to the eye via invasive methods such as direct drug injection into the vitreous humor or subconjunctival injections. Invasive methods can cause discomfort for the patient and can also lead to complications that are even more serious than the disease being treated. In most cases, topical or systemic administration is used to treat posterior diseases despite limited bioavailability from these formulations. There is also a need for sustained retention of drugs administered by topical administration onto the ocular surface since many diseases including inflammatory or infectious diseases require a greater drug concentration than can be achieved by infrequent topical administration due to issues with rapid clearance.

In the past few decades, research has focused on drug loaded nanoparticles, such as liposomes, micelles, dendrimers and polymersomes. Relatively few drug carriers have been approved for use in humans, which suggests that better strategies and materials may be required to generate successful nanomedicines. Traditional drug delivery systems have a number of deficiencies including a lack of targeted delivery, high toxicity, low cellular uptake, and poor biocompatibility. Therefore, there is a need in the art for improved drug delivery systems targeted to parts of the eye.

SUMMARY

Disclosed herein are novel methods and compositions for targeting therapeutics to specific cells. One aspect relates to a therapeutic agent comprising an elastin-like peptide (ELP) component and a ligand selected from the group consisting of mIgA and knob. Previous reports indicated that the fiber knob of adenovirus serotype 5 (Ad5) exhibits a high efficiency of internalization in liver after intravenous injection in mice (J. Virol. 78:6431-6438 (2004)). Both hepatocytes and lacrimal gland acinar cells (LGACs), also very efficiently transduced with Ad5 in a unique fiber-dependent pathway, display a very high level of coxsackie-adenovirus receptor (CAR) expression. Although CAR remains surface-associated in most cells, Applicants' research shows internalization of Ad5 in these cells is through a CAR-mediated and fiber-dependent endocytic pathway (J. Virol. 80:11833-11861 (2006)).

To develop new treatments for diseases of the lacrimal gland, new drug vehicles are required that are biocompatible, biodegradable and easily modified with bioactive peptides. An emerging approach to this challenge employs genetically engineered polypeptides to drive the assembly of nanostructures. Elastin-like-polypeptides possess unique phase transition behavior, that mediates self-assembly of nanoparticles.

A second aspect relates to a therapeutic agent comprising an elastin-like peptide (ELP) component and a ligand; wherein the ligand specifically binds to a receptor selected from the group consisting of CAR (GenBank acc.no. AF 200465.1) and pIgR (NCBI Reference Sequence NM_002644.3).

A further aspects relates to a method for delivering a therapeutic agent comprising an elastin-like peptide (ELP) to a cell, said method comprising: administering an (ELP) component and a ligand component to the cell; wherein the ligand component specifically binds to a receptor selected from the group consisting of CAR and pIgR.

Still further, there is provided a method for delivering a therapeutic agent comprising an elastin-like peptide (ELP) to a cell, said method comprising: administering an (ELP) component and a ligand component to the cell; wherein the ligand component is selected from the group consisting of mIgA and knob.

In another aspect, a method for delivering a drug to the luminal area of the lacrimal gland by transcytosis is provided, the method comprising, consisting essentially of, or yet further consisting of, contacting the lacrimal gland with one or more of a drug delivery agent, a polynucleotide, or a composition, as described herein, wherein the ligand component specifically binds to a CAR and/or pIgR receptor; and/or wherein the ligand component is mIgA and/or knob. The contacting can be in vitro or in vivo. In one embodiment, the drug is in contact with the ocular surface of the eye. Transcytosis allows the durg to have access to the ocular surface of the eye. The transcytosis property enables treatment of the surface of the eye for a variety of conditions like dry eye, scleritis, and the like.

In yet another aspect, provided is a method for treating a disease of the lacrimal gland, comprising, or alternatively consisting essentially of, or yet further consisting of, administering to a patient in need of such treatment one or more of a drug delivery agent, a polynucleotide, or a compositions, wherein the ligand component specifically binds to a CAR and/or pIgR receptor; and/or wherein the ligand component is mIgA and/or knob, thereby treating the patient. In one aspect, the disease is cancer.

In certain embodiments, the cell is any cell that expresses a CAR or pIGR receptor. Non-limiting examples include liver, heart, lacrimal gland, salivary gland, lung, brain, pancreatic acinar tissue, prostate or mucosal cells. In a related embodiment, the cell is the lacrimal acinar cell of the lacrimal gland (LGAC). CAR is detected in liver and lacrimal gland as well as in human umbilical vein endothelial cells and pancreatic acinar tissue (acinar cells and islets), as well as in prostate. Most mucosal epithelial cells display pIgR including the cells lining the gut, pulmonary epithelial cells, acinar cells (salivary, lacrimal gland) and other barrier epithelial tissues responsible for maintaining mucosal immunity. Accordingly, in one embodiment, the drug is released from interstitial to luminal surfaces on a mucosal epithelial cell.

BRIEF DESCRIPTION OF THE FIGURES

FIG. 18A shows the Cryo-transmission electron microscopy (TEM) imaging of S48148 and Knob-S48148 (Scale bar: 100 nm) and FIG. 18B shows the average partic protein or peptide therefore also refers to a protein or peptide, free from the environment in which it may naturally occur.

Figure 1:
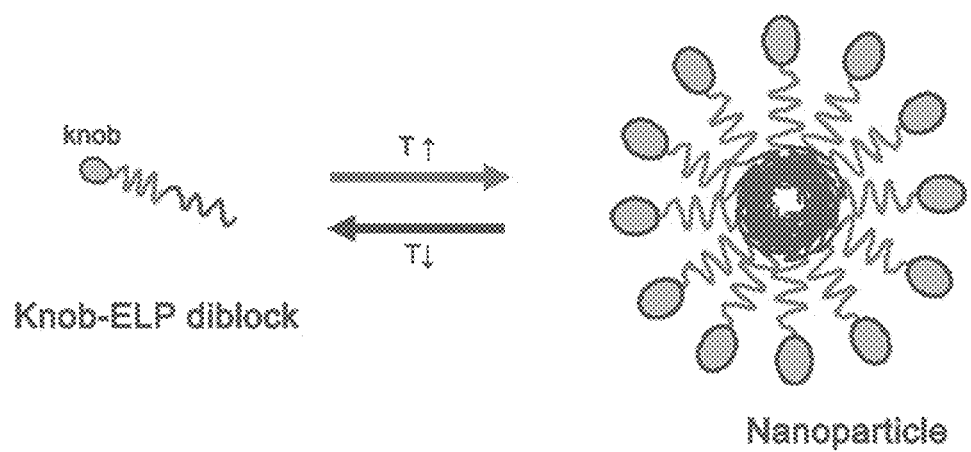
FIG. 1 is a schematic representation of knob-ELP fusion peptides. Full-length knob was expressed at the N-terminus of diblock ELPs. A thrombin cleavage site was engineered between the knob domain and the diblock ELP. The designed diblock knob-ELP can assemble into a nanoparticle, mediated by the first ELP phase transition of the diblock ELP. Above the first transition temperature, knob-ELP will reversibly self-assemble into a nanoparticle.

The term "therapeutic" refers to an agent or component capable of inducing a biological effect in vivo and/or in vitro. The biological effect may be useful for treating and/or preventing a condition, disorder, or disease in a subject or patient. A therapeutic may include, without limitation, a small molecule, a nucleic acid, or a polypeptide.

The term "coxsackievirus and adenovirus receptor" or "CAR" refers to a high affinity receptor that is present in many human tissues, including liver, heart, lacrimal gland, salivary gland, lung, and brain, pancreas and prostate.

The term "Polymeric Immunoglobulin Receptor" or "pIgR" refers to a high affinity receptor that is expressed by human mucosal cells.

"LGAC" or "lacrimal gland acinar cell" is a specific cell type of the lacrimal gland that expresses CAR and pIgR on the cell surface. These cells are also sometimes referred to lacrimal acinar epithelial cells.

This disclosure relates to genetically engineered polypeptide nanoparticles targeted to lacrimal gland acinar cells. To develop new treatments for disease of the lacrimal gland, new drug carriers are required that are biocompatible and easily modified with bioactive peptides. An emerging solution to this challenge utilizes genetically engineered polypeptides to drive the assembly of nanostructures. Elastin-like-polypeptide engages in a unique phase transition behavior, which can mediate self-assembly of nanoparticles. Described herein is a class of diblock ELP fusion proteins with high affinity peptides which are intended for targeting of lacrimal gland acinar cells (LGAC). The diblock mIgA-ELP fusion proteins are able to self assemble to nanoparticles, which can be utilized for gene therapy and drug delivery to LGAC and other mucosal epithelial cells.

As used herein, the term "biological equivalent thereof" is used synonymously with "equivalent" unless otherwise specifically intended. When referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 60%, or 65%, or 70%, or 75%, or 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, a biological equivalent is a peptide encoded by a nucleic acid that hybridizes under stringent conditions to a nucleic acid or complement that encodes the peptide. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide or polynucleotide region (or a polypeptide or polypeptide region) having a certain percentage (for example, about 60%, 65%, 70%, 75%, 80%, 85%, 90%, 95% or 97%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is a program of BLAST®, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

An "equivalent" of a polynucleotide or polypeptide refers to a polynucleotide or a polypeptide having a substantial homology or identity to the reference polynucleotide or polypeptide. In one aspect, a "substantial homology" is greater than about 60%, 65%, 70%, 75%, 80%, 85%, 90%, 95% or 98% homology.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Regulatory polynucleotide sequences" intends any one or more of promoters, operons, enhancers, as known to those skilled in the art to facilitate and enhance expression of polynucleotides.

An "expression vehicle" is a vehicle or a vector, non-limiting examples of which include viral vectors or plasmids, that assist with or facilitate expression of a gene or polynucleotide that has been inserted into the vehicle or vector.

A "delivery vehicle" is a vehicle or a vector that assists with the delivery of an exogenous polynucleotide into a target cell. The delivery vehicle may assist with expression or it may not, such as traditional calcium phosphate transfection compositions.

A "composition" is intended to mean a combination of active agent and another compound or composition, inert (for example, a solids support or pharmaceutically acceptable carrier) or active, such as an adjuvant.

A "pharmaceutical composition" is intended to include the combination of an active agent with a carrier, inert or active, making the composition suitable for diagnostic or therapeutic use in vitro, in vivo or ex vivo.

"An effective amount" refers to the amount of an active agent or a pharmaceutical composition sufficient to induce a desired biological and/or therapeutic result. That result can be alleviation of the signs, symptoms, or causes of a disease, or any other desired alteration of a biological system. The effective amount will vary depending upon the health condition or disease stage of the subject being treated, timing of administration, the manner of administration and the like, all of which can be determined readily by one of ordinary skill in the art.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

As used herein, to "treat" further includes systemic amelioration of the symptoms associated with the pathology and/or a delay in onset of symptoms. Clinical and subclinical evidence of "treatment" will vary with the pathology, the subject and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intrapentoneal, intravenous and by inhalation. An agent of the present invention can be administered for therapy by any suitable route of administration. It will also be appreciated that the preferred route will vary with the condition and age of the recipient, and the disease being treated.

The agents and compositions of the present invention can be used in the manufacture of medicaments and for the treatment of humans and other animals by administration in accordance with conventional procedures, such as an active ingredient in pharmaceutical compositions.

As used herein, the term "detectable label" intends a directly or indirectly detectable compound or composition that is conjugated directly or indirectly to the composition to be detected, e.g., N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, *Lucifer* Yellow, a fluorescent label sold under CASCADE BLUE®, and a fluorescent label sold under TEXAS RED®. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Elastin-Like Polypeptides (ELPs)

Elastin-like-polypeptides (ELPs) are a genetically engineered polypeptide with unique phase behavior (see for e.g. S. R. MacEwan, et al., Biopolymers 94(1) (2010) 60-77) which promotes recombinant expression, protein purification and self-assembly of nanostructures (see for e.g. A. Chilkoti, et al., Advanced Drug Delivery Reviews 54 (2002) 1093-1111). ELPs are artificial polypeptides composed of repeated pentapeptide sequences, $(VPGXG)_n$ (SEQ ID. NO: 1) derived from human tropoelastin, where X is the "guest residue" Which is any amino acid. In one embodiment, X is any amino acid except proline. This peptide motif displays rapid and reversible de-mixing from aqueous solutions above a transition temperature, $T_t$. Below $T_t$, ELPs adopt a highly water soluble random coil conformation; however, above $T_t$, they separate from solution, coalescing into a second aqueous phase. The $T_t$ of ELPs can be tuned by choosing the guest residue and ELP chain length as well as fusion peptides at the design level (see for e.g. MacEwan S R, et al., Biopolymers 94(1): 60-77). The ELP phase is both biocompatible and highly specific for ELPs or ELP fusion proteins, even in complex biological mixtures. Genetically engineered ELPs are monodisperse, biodegradable, non-toxic. Throughout this description, ELPs are identified by the single letter amino acid code of the guest residue followed by the number of repeat units, n. For example, S48I48 represents a diblock copolymer ELP with 48 serine (S) pentamers ([VPGSG]$_{48}$, SEQ ID. NO: 2) at the amino terminus and 48 isoleucine (I) pentamers ([VPGIG]$_{48}$, SEQ ID. NO: 3) at the carboxy terminus. A "diblock" as used herein refers to an ELP with two blocks of repeated polypeptide sequence. For example, the diblock (VPGSG)$_{48}$ (VPGIG)$_{48}$ (SEQ ID. NO: 12) comprises 48 repeated units of a polypeptide having the sequence VPGSG (SEQ ID NO: 2) and 48 repeated units of a polypeptide having the sequence VPGIG (SEQ ID. NO: 3). In one embodiment, the drug delivery agent comprises a polypeptide with the sequence of SEQ ID. NO: 12.

In further embodiments, the drug delivery agent comprises, a consisting essentially of, or yet consists of, a polypeptide with the sequence (VPGSG)$_{96}$ (SEQ ID. NO: 13) or (VPGIG)$_{96}$ (SEQ ID. NO: 14) or a biological equivalent thereof Described herein are ELP fusion proteins, which can be self assembled into nanoparticles. The diameter of the nanoparticle can be from about 1 to about 1000 nm or from about 1 to about 500 nm, or from about 1 to about 100 nm, or from about 1 to about 50 nm, or from about 20 to about 50 nm, or from about 30 to about 50 nm, or from about 35 to about 45 nm. In one embodiment, the diameter is about 40 nm. These nanoparticles can be high efficiently internalized into LGAC. The fusion proteins are composed of elastin-like-polypeptides and high affinity polypeptides. These fusion proteins can be expressed from a variety of expression systems known to those skilled in the art and easily purified by the phase transition behavior of ELPs. These ELP fusion proteins are able to conjugate small molecules, such as, for example, chemotherapeutic agents, anti-inflammation agents, antibiotics and polypeptides and other water soluble drugs. In addition, the ELP nanoparticles are useful for carrying DNA, RNA, protein and peptide-based therapeutics.

ELPs have potential advantages over chemically synthesized polymers as drug delivery agents. First, because they are biosynthesized from a genetically encoded template, ELPs can be made with precise molecular weight. Chemical synthesis of long linear polymers does not typically produce an exact length, but instead a range of lengths. Consequently, fractions containing both small and large polymers yield mixed pharmacokinetics and biodistribution. Second, ELP biosynthesis produces very complex amino acid sequences with nearly perfect reproducibility. This enables very precise selection of the location of drug attachment. Thus drug can be selectively placed on the corona, buried in the core, or dispersed equally throughout the polymer. Third, ELP can self assemble into multivalent nanoparticles that can have excellent site-specific accumulation and drug carrying properties. Fourth, because ELP are designed from native amino acid sequences found extensively in the human body they are biodegradable, biocompatible, and tolerated by the immune system. Fifth, ELPs undergo an inverse phase transition temperature, $T_t$, above which they phase separate into large aggregates. By localized heating, additional ELP can be drawn into the target site, which may be beneficial for increasing drug concentrations.

A therapeutic such as a drug, for example, may be attached to the ELP through cysteine, lysine, glutamic acid or aspartic acid residues present in the polymer. In some embodiments, the cysteine, lysine, glutamic acid or aspartic acid residues are generally present throughout the length of the polymer. In some embodiments, the cysteine, lysine, glutamic acid or aspartic acid residues are clustered at the end of the polymer. In some embodiments of the presently described subject matter, therapeutics are attached to the cysteine residues of the ELP using thiol reactive linkers. In some embodiments of the presently described subject matter, therapeutics are attached to the lysine residues of the high molecular weight polymer sequence using NHS (N-hydroxysuccinimide) chemistry to modify the primary amine group present on these residues. In some embodiments of the presently described subject matter, therapeutics are attached to the glutamic acid or aspartic acid residues of the ELP using EDC (1-Ethyl-3-[3-dimethylaminopropyl]carbodiimide Hydrochloride) chemistry to modify the carboxylic acid group present on the ELP residues.

The therapeutic associated with the ELP may be hydrophobic or hydrophilic. Which the drug is hydrophobic, attachment to the terminus of the ELP may facilitate formation of the multivalent nanoparticle. The number of drug particles attached to the ELP can be from about 1 to about 30, or from about 1 to about 10, or about 1, 2, 3, 4, 5, 6, 7, 8, 9, or 10. In some embodiments, the attachment points for a therapeutic are equally distributed along the backbone of the ELP, and the resulting drug-ELP is prevented from forming nanoparticle structures under physiological salt and temperature conditions.

In addition to therapeutics, the ELPs may also be associated with a detectable label that allows for the visual detection of in vivo uptake of the ELPs. Suitable labels include, for example, fluorescein, rhodamine, tetramethylrhodamine, eosin, erythrosin, coumarin, methyl-coumarins, pyrene, Malacite green, a detectable label sold under ALEXA-FLUOR®, stilbene, Lucifer Yellow, CASCADE BLUE®, and TEXAS RED®. Other suitable optical dyes are described in Haugland, Richard P. (1996) MOLECULAR PROBES™ Handbook (which is a Guide to Fluorescent Probes and Labeling Technologies).

In certain embodiments, the ELP components include polymeric or oligomeric repeats of the pentapeptide VPGXG (SEQ ID. NO: 1), where the guest residue X is any amino acid, that in one aspect, excludes proline. X may be a naturally occurring or non-naturally occurring amino acid. In some embodiments, X is selected from alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine. In some embodiments, X is a natural amino acid other than proline or cysteine.

The guest residue X may be a non-classical (non-genetically encoded) amino acid. Examples of non-classical amino acids include: D-isomers of the common amino acids, 2, 4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general.

Selection of X is independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In each embodiment, the structural units, or in some cases polymeric or oligomeric repeats, of the ELP sequences may be separated by one or more amino acid residues that do not eliminate the overall effect of the molecule, that is, in imparting certain improvements to the therapeutic component as described. In certain embodiments, such one or more amino acids also do not eliminate or substantially affect the phase transition properties of the ELP component (relative to the deletion of such one or more amino acids).

The ELP component in some embodiments is selected or designed to provide a $T_t$ ranging from about 10 to about 80° C., such as from about 35 to about 60° C., or from about 38 to about 45° C. In some embodiments, the $T_t$ is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the $T_t$ is below the body temperature (e.g., <37° C.) to provide alternative advantages, such as in vivo formation of a drug depot for sustained release of the therapeutic agent.

The $T_t$ of the ELP component can be modified by varying ELP chain length, as the Tt generally increases with decreasing MW. For polypeptides having a molecular weight >100,000, the hydrophobicity scale developed by Urry et al. (PCT/US96/05186, which is hereby incorporated by reference in its entirety) is preferred for predicting the approximate $T_t$ of a specific ELP sequence. However, in some embodiments, ELP component length can be kept relatively small, while maintaining a target $T_t$, by incorporating a larger fraction of hydrophobic guest residues (e.g., amino acid residues having hydrophobic side chains) in the ELP sequence. For polypeptides having a molecular weight <100,000, the $T_t$ may be predicted or determined by the following quadratic function: $T_t=M_0+M_1X+M_2X^2$ where X is the MW of the fusion protein, and $M_0=116.21$; $M_1=-1.7499$; $M_2=0.010349$.

While the $T_t$ of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, and half-life of the molecule.

Ligands

In certain embodiments of the invention, the therapeutic agent comprises an ELP component fused or conjugated to a LGAC-targeted ligand. A LGAC-targeted ligand is a peptide, polypeptide, or molecule that targets the ELP to the LGAC. In one embodiment, the ligand component of the drug delivery agent described herein is the adenovirus knob domain, which is a LGAC-targeted ligand. This domain is represented by the protein sequence: GAITVGNKNNDKLTLWTTPAPSPNCRLNAEKDAK-LTLVLTKCGSQILATVSVLAVKGSL APISGTVQSAHL-IIRFDENGVLLNNSFLDPEYWNFRNGDLTEGTAYT-NAVGFMPNLSAY PKSHGKTAKSNIVSQVYLNG-DKTKPVTLTITLNGTQETGDTTPSAYSMSFSWD-WSGHN YINEIFATSSYTFSYIAQE (SEQ ID. NO: 4), or a biological equivalent thereof. The term "biological equivalent" is defined above. In one aspect, a biological equivalent is a peptide encoded by a nucleic acid that hybrizes to a nucleic acid that encodes the LGAC-targeted ligand 2 or its complement under conditions of a high stringency hybridization reaction, that is performed at about 60° C. in about 1×SSC that has substantial identical biological activity to the above-noted sequence. In one embodiment, the knob ligand comprises a polypeptide having the sequence of SEQ ID. NO: 4 or a biological equivalent thereof.

In certain embodiments, the ELP comprises knob or a polypeptide with at least 80% identity to knob. Alternatively, the polypeptide has about at least 85% or about at least 90% or about at least 95%, or about at least 99% identity to knob.

In further embodiments, the ELP comprises a mIgA ligand or double mIgA ligand. This ligand is represented by the amino acid sequence: TWASRQEPSQGTTTFAVTS (SEQ ID. NO: 5) or a biological equivalent thereof. In one embodiment, the mIgA ligand comprises a polypeptide having the sequence of SEQ ID. NO: 5 or a biological equivalent thereof. The term "biological equivalent" is defined above. In one aspect, a biological equivalent is a peptide encoded by a nucleic acid that hybrizes to a nucleic acid that encodes the mIgA ligand or double mIgA ligand or its complement under conditions of a high stringency hybridization reaction, that is performed at about 60° C. in about 1×SSC that has substantial identical biological activity to the above-noted sequence. In certain embodiments, the ELP comprises the mIgA ligand or a polypeptide with at least 80% identity to mIgA. Alternatively, the polypeptide has about at least 85% or about at least 90% or about at least 95%, or about at least 99% identity to mIgA. The term "mIgA" refers to the pIgR-binding site in the Cα3 domain of dimeric human IgA. The Cα3 domain is represented by the protein sequence: RP EVHLLPPPSE ELALNELVTL TCLARGFSPK DVLVRWLQGS QELPREKYLT WAS-RQEPSQG TTTFAVTSIL RVAAEDWKKG DTFSCMVGHE ALPLAFTQKT ID (SEQ ID. NO: 6) (See for e.g. Frank W. Putnam, et al. J. Biol. Chem. 254, 2865-2874).

Expression of Recombinant Proteins

ELPs and other recombinant proteins described herein can be prepared by expressing polynucleotides encoding the polypeptide sequences of this invention in an appropriate host cell, i.e., a prokaryotic or eukaryotic host cell This can be accomplished by methods of recombinant DNA technology known to those skilled in the art. It is know to those skilled in the art that modifications can be made to any peptide to provide it with altered properties. Polypeptides of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that beta-turn spiral secondary structure or random secondary structure is preferred.

The ELPs can be expressed and purified from a suitable host cell system. Suitable host cells include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. In one embodiment, the host cell is *E. coli*. The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

Protein Purification

The phase transition behavior of the ELPs allows for easy purification. The ELPs may also be purified from host cells using methods known to those skilled in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC. In the case of ELP compositions protein purification may also be aided by the thermal transition properties of the ELP domain as described in U.S. Pat. No. 6,852,834.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Pharmaceutical Compositions

Pharmaceutical compositions are further provided. The compositions comprise a carrier and ELPs as described herein. The carriers can be one or more of a solid support or a pharmaceutically acceptable carrier. In one aspect, the compositions are formulated with one or more pharmaceutically acceptable excipients, diluents, carriers and/or adjuvants. In addition, embodiments of the compositions include ELPs, formulated with one or more pharmaceutically acceptable auxiliary substances.

The invention provides pharmaceutical formulations in which the one or more of an isolated polypeptide of the invention, an isolated polynucleotide of the invention, a vector of the invention, an isolated host cell of the invention, or an antibody of the invention can be formulated into preparations for injection in accordance with the invention by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g. a Type IV Pilin protein (see Jurcisek and Bakaletz (2007) J. of Bacteriology 189(10):3868-3875) and antibacterial agents.

Aerosol formulations provided by the invention can be administered via inhalation. For example, embodiments of the pharmaceutical formulations of the invention comprise a compound of the invention formulated into pressurized acceptable propellants such as dichlorodifluoromethane, propane, nitrogen and the like.

Embodiments of the pharmaceutical formulations of the invention include those in which the ELP is formulated in an injectable composition. Injectable pharmaceutical formulations of the invention are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations of the invention.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Routes of administration applicable to the methods and compositions described herein include intranasal, intramuscular, subcutaneous, intradermal, topical application, intravenous, nasal, oral, inhalation, intralacrimal, retrolacrimal profusal along the duct, intralacrimal, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In one embodiment, the composition comprising the ELP is administered intralacrimally through injection. In further embodiments, the composition is administered systemically, topically on top of the eye, by retrolacrimal profusion, or intranasally.

Treatment of Disease

Methods and compositions disclosed herein are useful in treating disorders of the eye. The lacrimal gland acinar cell targeted ELPs provide a site-specific target therapeutic. Accordingly, these ELP nanoparticles may be useful to encapsulate or attach drugs for treating disorders localized to the eye. By way of example, these disorders can include, age-related macular degeneration, Sjögren's syndrome, autoimmune exocrinopathy, diabetic retinopathy, graft versus host disease (exocrinopathy associated with) retinal venous occlusions, retinal arterial occlusion, macular edema, postoperative inflammation, uveitis retinitis, proliferative vitreoretinopathy and glaucoma. In one embodiment, the disease is Sjögren's syndrome. In another embodiment, the disease is keratoconjunctivitis sicca (dry eye). In another embodiment the disease is scleritis. In another embodiment the disease is glaucoma.

Combination Treatments

Administration of the therapeutic agent or substance of the present invention to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

Example 1

ELPs Comprising Targeting Ligands

Since discovered a half century ago, human adenovirus has attracted attention because different types cause significant levels of respiratory, ocular, and gastrointestinal disease. Because of its pathological effects, a significant amount of information is therefore available on its mode of interaction with cells. Adenovirus serotype 2 and serotype 5 within subgroup C, the best understood types of this virus, attach to cells through the initial binding of the fiber protein to the cell-surface coxsackievirus and adenovirus receptor (CAR). CAR is a 46-kDa high affinity receptor that is present in many human tissues, including liver, heart, lacrimal gland, lung, and brain and which is thought to function as a cell adhesion protein. Upon surface binding, adenovirus entry in most cells is facilitated through interaction of an additional adenoviral capsid protein, the penton base, with integrin receptors on the plasma membrane, a process facilitating efficient entry via endocytosis. This mechanism, which occurs in cells expressing the most abundant CAR protein in the body, has been reported to deliver a region of the fiber capsid protein, the knob, to a subcellular degradative compartment. After entry, through either fiber/knob- or penton-dependent interactions, mechanisms have been described for the subsequent interactions between the virus and other intracellular transport machinery, which facilitate efficient trafficking of the viral DNA to the nucleus. For these and other reasons, most notably the ability of adenovirus to transduce non-dividing cells, adenovirus serotype 5 and other serotypes have been explored as vectors for gene therapy. However, despite their relatively efficient cellular endocytosis and gene transfer, viral vectors in general have intrinsic drawbacks, such as limited opportunities for repeat administrations due to acute inflammatory responses and delayed humoral or cellular immune responses. In addition, some viral vectors integrate DNA into the genome, resulting in insertional mutagenesis.

In the past few decades, numerous research groups have focused on drug carriers, such as liposomes, micelles, dendrimers, and polymersomes. Relatively few drug carriers have been approved for use in humans, which suggests that better strategies and materials may be required to generate successful nanomedicines. One emerging strategy is to design genetically engineered protein polymers that self-assemble directly into nanoparticles. For example, the elastin-like-polypeptides (ELP) are a genetically engineered polypeptide with unique phase behavior, which promotes recombinant expression, protein purification and self-assembly of nanostructures. Genetically engineered ELPs are biodegradable and biocompatible. ELPs are composed of the repeated amino acid sequence $(VPGXG)_n$ (SEQ ID. NO: 1), where the hydrophobicity of X determines the polypeptide phase behavior. Exemplified herein, ELPs are identified by the single letter amino acid code of the guest residue followed by the number of repeat units, n. For example, S48I48 represents a diblock copolymer ELP with 48 serine (S) pentamers at the amino terminus and 48 isoleucine (I) pentamers at the carboxy terminus.

Lacrimal acinar epithelial cells exhibit a unique fiber-dependent internalization mechanism for adenovirus type 5, and this internalization mechanism can be recapitulated by the knob domain of the fiber protein. This mechanism seems to operate in hepatocytes as well to enable internalization of free knob protein to intracellular degradative compartments. This is in contrast to other demonstrations that fiber is responsible only for the initial binding of adenovirus to the cell via CAR, and not for internalization, which is driven by the penton base capsid protein and integrin receptors on the plasma membrane, a process facilitating efficient entry. Some studies have recently shown that CAR, which is a cell adhesion protein and thought to be largely surface associated, can in fact be endocytosed. Altogether these studies suggest that in certain cells, such as acinar cells and hepatocytes where CAR is highly abundant, that a subpopulation may serve as an internalization receptor when bound to fiber or knob proteins. The physiological relevance of this endocytic population of CAR in these cells is so far unknown. To exploit this apparent CAR internalization pathway and high affinity interaction with viral proteins for drug delivery while minimizing the use of the entire viral capsid, described herein is the development of a simple gene product that assembles nanoparticles decorated with the knob domain of adenovirus fiber protein. The most significant advantages of this platform include: (i) compatibility with genetic engineering; (ii) no bioconjugate chemistry is required to link fusion proteins to the nanoparticle; (iii) and the resulting polypeptides assemble into nanoparticles that are monodisperse, multivalent, and biodegradable. These particles are predominantly composed of diblock copolymers of ELP. ELP block copolymers self-assemble multimeric nanoparticles above a transition temperature that can be controlled by adjusting their hydrophobicity and molecular weight (FIG. 1). Above the critical temperature for the ELP diblock copolymer, the knob-ELP fusion protein also assembles nanoparticles. It was investigated whether nanocarriers displaying the knob domain may exhibit selective internalization into tissues expressing unique CAR-dependent endoyctosis of fiber and knob. Described herein are the biophysical properties and cellular uptake of a knob-ELP, which self assembles nanoparticles that have potential applications for drug delivery and gene therapy.

Materials and Reagents

TB dry powder growth medium was purchased from MO BIO Laboratories, Inc. (Carlsbad, Calif.). NHS-Rhodamine was purchased from Thermo Fisher Scientific (Rockford, Ill.). A kit for cleaving a fusion protein sold under Thrombin CLEANCLEAVE™ Kit, Polyethylenimine, Copper Chloride and insulin were obtained from Sigma-Aldrich (St. Louis, Mo.). The knob domain gene sequence was ordered from Integrated DNA Technologies (Coralville, Iowa). LYSOTRACKER® Green CN 26 was purchased from Invitrogen (Carlsbad, Calif.). Goat anti-mouse CAR antibody was obtained from R&D Systems (Minneapolis, Minn.). IRDYE® 800-conjugated donkey anti-goat second antibody was purchased from Rockland (Gilbertsville, Pa.). Blocking buffer was purchased from Li-COR Biosciences (Lincoln, NB). a purification kit sold under QIAPREP® Spin Miniprep Kit and a gel extraction kit sold under QIAQUICK® Gel Extraction Kit were purchased from Qiagen (Valencia, Calif.).

Knob-ELP Vector Design

The plasmids encoding ELP were designed similarly to those reported previously (see, for e.g., A. Chilkoti, et al., Advanced Drug Delivery Reviews 54 (2002) 1093-1111 and J. R. McDaniel, et al., Biomacromolecules 11(4) (2010) 944-952 which is incorporated by reference). The knob domain gene sequence was designed with restriction enzyme NdeI and BamHI at 5' and 3' of the knob gene respectively. A thrombin amino acid recognition site (GLVPRGS; SEQ ID. NO: 7) was incorporated between the knob sequence and the ELP sequence. A recognition site for BseRI was also incorporated to facilitate the insertion of ELP genes with complementary two base pair 5' overhang(s). The plasmids containing genes that encode for ELP and knob were double digested by BseRI and BssHII, and the DNA pieces containing ELP and knob were purified using a gel extraction kit and then ligated together. Successful clones were confirmed by diagnostic DNA digestion, DNA sequencing, and mass spectrometry of the polypeptide gene products.

Purification of ELP Fusion Proteins

*E. coli* strain BLR (Novagen Inc., Milwaukee, Wis.) was transformed with the modified pET-25(+) expression vectors containing the ELP or knob-ELP genes. The bacteria were grown overnight in 5 mL TB dry medium supplemented with 1 μg/mL ampicillin in an orbital shaker at 37° C. Then bacteria were centrifuged down, and the pellet was resuspended in 2 liters TB dry medium and cultured for 24 hours in an orbital shaker at 37° C. The bacteria were again harvested by centrifugation at 4° C. and resuspended in phosphate buffer saline (PBS). The bacteria were lysed by discontinuous pulsed ultrasonication in an ice-water bath. The insoluble debris was removed from the lysate by centrifugation and nucleic acids were precipitated by adding polyethylenimine (0.5% w/v final concentration) and removed by centrifugation at 4° C. From the clarified bacterial lysates, the ELPs and knob-ELPs were purified by inverse transition cycling (ITC), which has been described previously [20-22]. Briefly, ELP solutions were warmed at room temperature and NaCl was added (1-3 M final concentration) to induce the ELP phase separation. The aggregated ELP fusion polypeptides were separated from the lysate by centrifugation at room temperature. The ELP pellet was resolubilized in PBS within an ice-water bath. The resolubilized ELP solution was centrifuged at 4° C. to remove remaining aggregated proteins. It was previously reported that purification cycles were repeated for two to six rounds as needed to purify various ELP fusion proteins (See, for e.g., D. E. Meyer, et al., Nature Biotechnology 17 (1999) 1112-111520, and K. Trabbic-Carlson, et al., Protein Sci 13(12) (2004) 3274-3284 which is herein incorporated by reference). In this study, the purification cycle was repeated five times to remove nearly all of the contaminating *E. coli* proteins, which was essential because contaminants may aggregate during heating and bias the hydrodynamic radius. The purity of purified knob-ELP was measured using SDS-PAGE in a 10% gel. After electrophoresis, the gel was stained with Coomassie brilliant blue.

Characterization of Knob-ELP

As described above, the knob-ELP was designed as a fusion protein consisting of a knob domain and an ELP. To study these multifunctional polypeptides, they were characterized by non-denaturing PAGE, turbidometric analysis of their temperature-dependent phase behavior, and dynamic light scattering. Native fiber/knob proteins are trimeric; therefore, the ability of knob-ELPs to self-associate was characterized using non-denaturing PAGE. Knob-S48148 and recombinant knob was mixed with sample buffer without 2-mercaptoethanol, and then loaded onto a 10% polyacrylamide gel without SDS at 4° C. At this temperature, the ELP nanoparticles remain dissociated, which enables the polypeptides to enter the gel. After three hours of electrophoresis, the gel was stained with Coomassie brilliant blue.

To explore the temperature-dependent phase behavior of the ELPs, optical density and hydrodynamic radius were observed over a range of temperatures. Knob-S96, S48148 and knob-S48148 were diluted to 25 μM in PBS on ice and the absorbance at 350 nm was monitored with a DU800 UV-Vis spectrophotometer (Beckman Coulter, Brea, Calif.) at a temperature gradient of 1° C./minute. For dynamic light scattering studies, S48148 and knob-S48148 were diluted to 25 μM in PBS and passed through 20 nm membrane filters at 4° C., and BSA, a protein with a similar molecular to knob-S48148 was used as a control. Then 90 μL sample of was transferred into a 384 well microplate and covered with 20 μL mineral oil. The microplate and mineral oil were pre-chilled at 4° C. at least for 1 hour. The microplate was centrifuged at 4° C. to remove air bubbles from samples before and after addition of mineral oil. Then the sample was measured in a DynaPro plate reader (Wyatt Inc., Santa Barbara, Calif.) at temperature intervals of 1° C. The resulting hydrodynamic radii were collected and analyzed by Dynamics (Wyatt Inc., Santa Barbara, Calif.). The measurements were repeated three times and particle radius for BSA, S48148 and knob-S48148 at 15° C. and 37° C. were analyzed by a one-way analysis of variance ($R^2=1.000$, $p=10^{-20}$, n=18).

Thrombin Cleavage of Knob-ELP

A thrombin recognition site was designed between the knob domain and ELP sequence (Table 1), which was cleaved by thrombin (Sigma-Aldrich, St. Louis, Mo.). Thrombin immobilized on agarose beads was centrifuged to remove the storage buffer and washed with cleavage buffer (from the thrombin cleavage kit). The knob-S48148 was then diluted with cleavage buffer to 1 mg/mL and suspended with thrombin agarose slurry for 24 hours at room temperature. After incubation, the thrombin agarose beads were removed by centrifugation. The cleaved knob (21.7 kD) was resolved by SDS-PAGE and gels were stained with Coomassie brilliant blue. The SDS-PAGE gel was scanned with a Molecular Imager Gel Doc XR System (Bio-Rad, Hercules, Calif.) and analyzed with software Quantity one (Bio-Rad).

TABLE 1

Summary of Expressed Polypeptides

| Peptide label | *Amino acid sequence | **Critical aggregation temperature (20° C.) | Expected molecular weight (kD) | ***Measured molecular weight (kD) | ****Hydrodynamic radius (nm) at 37° C. |
|---|---|---|---|---|---|
| knob-S96 | knob-(VPGSG)$_{96}$Y (SEQ ID. NO: 8) | 68.2 | 60.179 | - | 5.3 |
| knob-I96 | knob-(VPGIG)$_{96}$Y (SEQ ID. NO: 9) | - | 62.682 | - | - |
| knob-S48I48 | knob-G(VPGSG)$_{48}$(VPGIG)$_{48}$Y (SEQ ID. NO: 10) | 19.5 | 61.431 | 61.241 | 21.7 |
| S48I48 | G(VPGSG)$_{48}$(VPGIG)$_{48}$Y (SEQ ID. NO: 10) | 26.5 | 39.643 | 39.670 | 23.7 |

*Knob amino acid sequence with thrombin cleavage site underlined:
GAITVGNKNNDKLTLWTTPAPSPNCRLNAEKDAKLTLVLTKCGSQILATVSVLAVKGSLAPISGTVQSAHLIIRFDENGV
LLNNSFLDPPEYWNFRNGDLTEGTAYTNAVGFMPNLSAYPKSHGKTAKSNIVSQVYLNGDKTKPVTLTITLNGTQETGDTT
PSAYSMSFSWDWSGHNYINEIFATSSYTFSYIAQE<u>GLVPRGSG</u> (SEQ ID. NO: 11)
**determined using optical density by UV-Vis spectrophotometer.
***determined using MALDI mass spectrometry.
****determined using dynamic light scattering.

Self-Assembly or Disassembly of Nanoparticles-Above/Below their Phrase Transition Temperatures

TABLE 2

Summary of Expressed Polypeptides

| Peptide | Amino acid sequence | Measured molecular weight (kDa) | Transition Temperature (° C.) T1 | T2 |
|---|---|---|---|---|
| S48I48 | G(VPGSG)$_{48}$(VPGIG)$_{48}$Y (SEQ ID. NO: 10) | 39.67 | 26.5 | 75 |
| knob-S48I48 | knob-G(VPGSG)$_{48}$(VPGIG)$_{48}$Y (SEQ ID. NO: 10) | 61.24 | 19.5 | 60 |

Conjugation with NHS-Rhodamine

To track cellular uptake, the ELPs S48I48 and knob-S48I48 were conjugated with a detectable label, NHS-Rhodamine (Thermo Fisher Scientific Inc, Rockford, Ill.) via covalent modification of primary amines at the amino end of the peptide. For S48I48, the only available amine is at the amino terminus; however, knob-S48I48 has an additional 11 lysine residues that may be sites of modification. The conjugation was performed in 100 mM borate buffer for 2 hours at 4° C., and the conjugated ELP was separated by size exclusion chromatography on a PD10 desalting column (GE Healthcare, Piscataway, N.J.).

Cellular Uptake of Knob-ELP/ELP

Hepatocytes were expected to be enriched in the CAR receptor, according to previous reports (see, for e.g., J. Xie, L. et al., J. Virol. 80(23) (2006) 11833-11851). To confirm this, a western blot was performed on a murine hepatocyte cell-line. CHO cells were used as a negative control. 2×10⁴ cells were mixed with SDS-PAGE sample buffer and heated above 95° C. for 5 minutes. CAR was detected by western blotting using a goat anti-mouse CAR antibody as the primary antibody and IRDYE® 800-conjugated donkey anti-goat antibody as the secondary antibody. The result was scanned using an imaging system sold under ODYSSEY® Imaging System (Li-COR, Lincoln, Nebr., USA) and quantified with a software sold under ODYSSEY® 1.1 software.

To observe uptake into mouse hepatocytes, cells were cultured on 35 mm glass coverslip-bottomed dishes with medium [(DMEM (4.5 g/L) containing 10% fetal bovine serum, g/ml insulin, and 0.02 [μg/ml epidermal growth factor]. Uptake studies were conducted when hepatocytes reached 70% confluence. After washing with warm fresh medium, hepatocytes were cultured in medium containing 10 μM of either S48I48 or knob-S48I48 conjugated with rhodamine, and 75 nM LYSOTRACKER® green. After 30 minutes incubation at 37° C., the cells were rinsed with warm fresh medium to remove the free knob-ELP/ELP in the medium. Next cells were incubated with 75 nM LYSOTRACKER® green in a 37° C. incubation chamber. The chamber is mounted on a Zeiss LSM 510 Meta confocal microscope system, which is equipped with argon and red and green HeNe lasers and mounted on a vibration-free table.

To demonstrate the specificity of knob-ELP internalization for the CAR pathway, hepatocytes were pre-bound with goat anti-mouse CAR antibody. After confirming that the goat anti-mouse CAR antibody has a high affinity with the mouse hepatocytes, the anti-mouse CAR antibody (0.2 mg/mL) was diluted with warm medium 10-fold and incubated with the hepatocytes for 30 minutes at 37° C. Knob-S48I48 conjugated with rhodamine was then added to the medium at a concentration of 10 μM. After 30 minutes incubation with knob-S48I48 and 75 nM LYSOTRACKER® green, the hepatocytes were rinsed, then incubated in fresh warm medium with 75 nM LYSOTRACKER® green and imaged as described above.

Example 2

Transcytosis of Knob-ELPs to Lacrimal Gland Acinar Lumen

Figure 13:
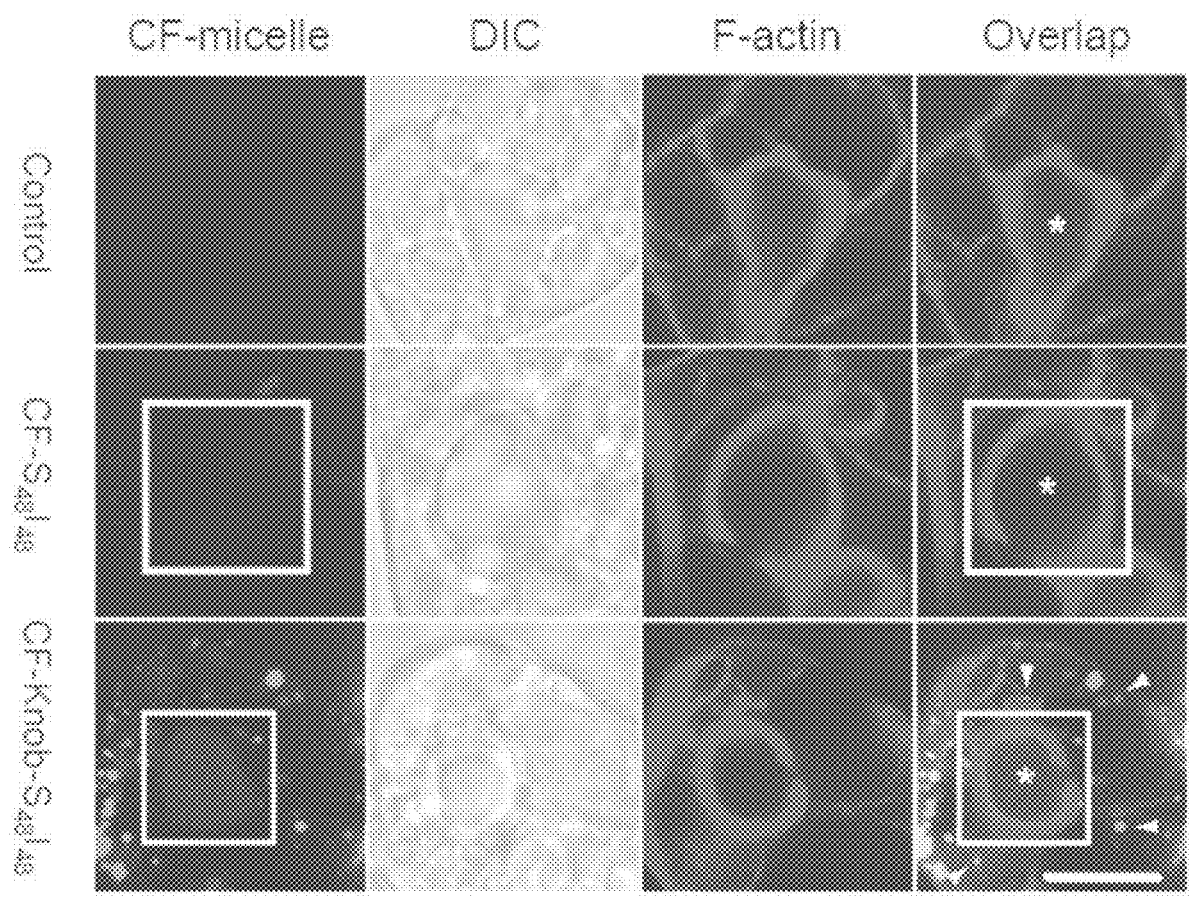
FIG. 13 shows intracellular uptake of carboxyfluorescein (CF)-conjugated ELPs in lacrimal gland acinar cells. Unlike CF-S48I48, CF-Knob-S48I48 exhibits strong internalization which was shown in green in reconstituted LGACs. Also endocytosed CF-Knob-S48I48 was transcytosed into reconstituted acinar lumen which was stained by expressed Lifeact-RFP proteins (red).

Intracellular uptake of carboxyfluorescein (CF)-conjugated ELPs in lacrimal gland acinar cells (LGACs) is shown in FIG. 13. Unlike CF-S48I48, CF-Knob-S48I48 exhibits strong internalization which was shown in green in reconstituted LGACs. FIG. 13 shows that endocytosed CF-Knob-S48I48 was transcytosed into reconstituted acinar lumen which was stained by expressed Lifeact-RFP proteins (red).

Figure 14:
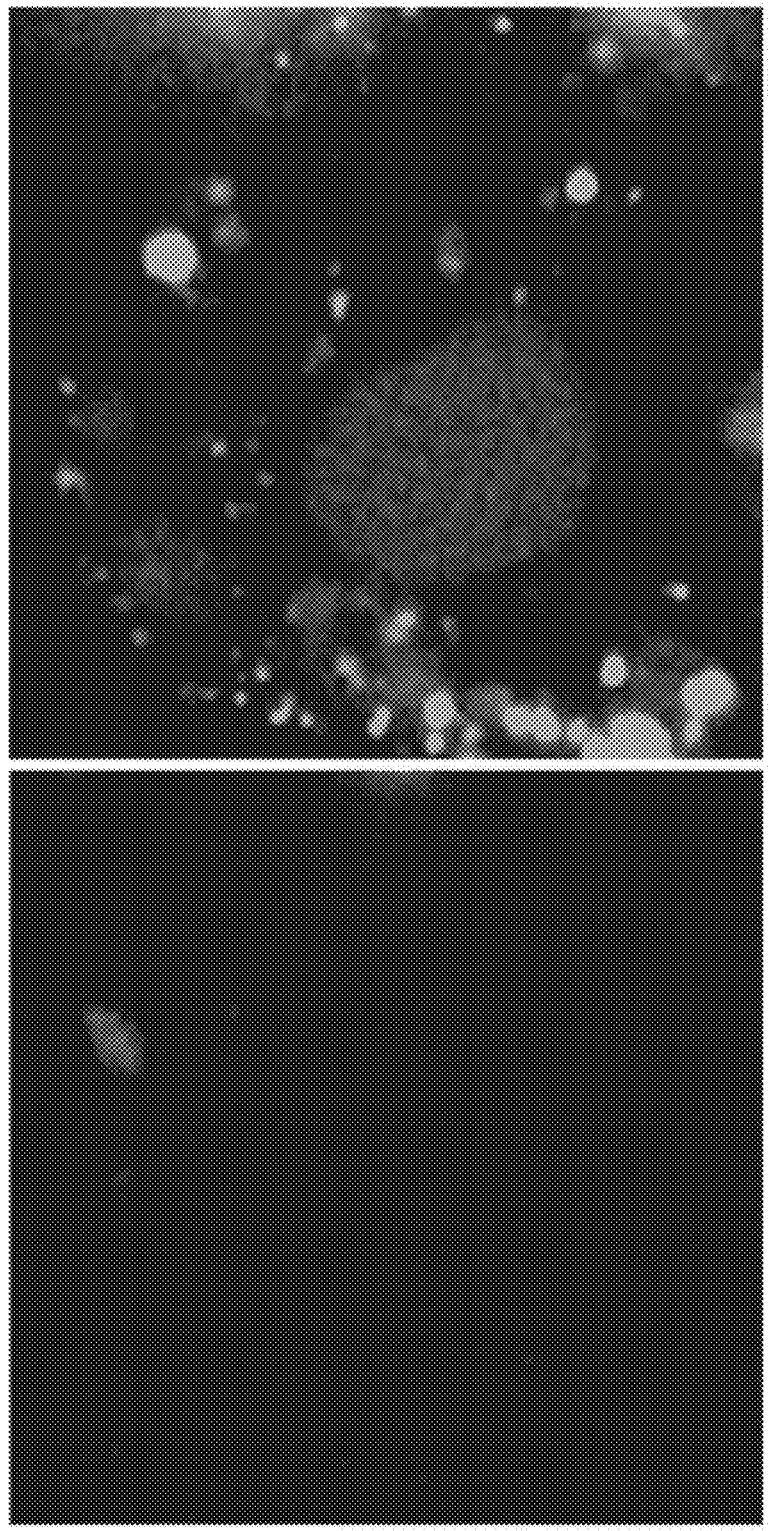
FIG. 14 shows lumen A (S48I48, left panel) and lumen B (Knob-S48I48, right panel). Arrowheads indicate internalized nanoparticles (Knob-S48148). The symbol "*" indicates lumen. Box indicates luminal area of LGACs. Scale bar represents 10 μm.

Lumen A (S48148) and lumen B (Knob-S48148) are shown in FIG. 14. Internalized knob-S48148 was transcytosed into the luminal area of LGACs as shown in lumen B.

Figure 17:
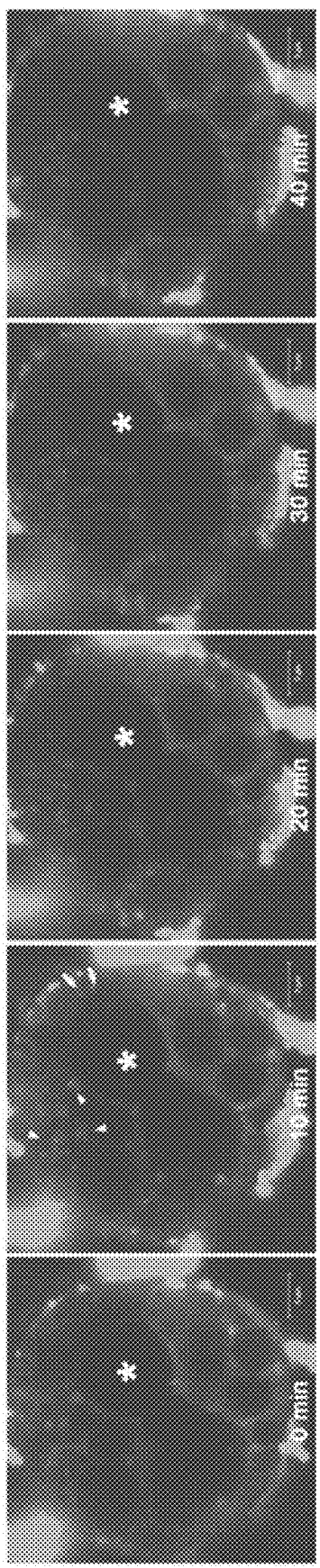
FIG. 17 shows the basal-to-apical transport of Cy5-Knob-S48148 in primary cultures of Lacrimal Gland Acinar Cells (LGACs).

In a separate experiment the basal-to-apical transport of Cy5-Knob-S48I48 in primary cultures of Lacrimal Gland Acinar Cells (LGACs) was observed. As shown in FIG. 17, uptake of Cy5-Knob-S48148 in LGACs with overexpressed RFP-Rab5a. Rabbit LGACs were transduced on day 2 with Adenovirus encoding RFP-Rab5a (red) in order to stain early endosome structures. After 16-18 hours LGACs were incubated with 30 μM Cy5-Knob-S48148 (green) at 37° C. for 10 min before imaging by confocal microscopy over 40 min. In FIG. 17, asterisks denote the acinar lumen., and the arrowheads indicate the dynamic fusion of early endosomes containing Cy5-Knob-S48I48 nanoparticles internalized from the basolateral membrane. The transcytosis experiments were conducted in primary rabbit lacrimal gland acinar cells (LGACs). LGACs were isolated and maintained in a laminin-based primary culture system and grown on the 35 mm petri dishes for 2 to 3 days. These culture conditions let LGACs reconstitute polarity, establish lumina, and format secretory vesicles. The dishes were pre-coated with commercial matrigel (BD Sciences, Franklin Lakes, N.J.). The dishes were incubated with 1 mL matrigel at 1:50 dilution with ice cold medium at 37° C. for 30 min and the dishes were emptied prior to adding cells. Female New Zealand White rabbits weighing between 1.8 and 2.2 kg were obtained from Irish Farms (Norco, Calif.). Before the experiment, the LGACs were pre-incubated at the second day with baculovirus encoding RFP-Rab5a overnight, which can indicate basolateral and apical early endosomes of rabbit LGACs. Cy5 labelled knob-S48148 (Cy5 knob-S48148) was utilized in the transcytosis experiment. 30 M Cy5-knob-S48148 diluted in the same medium as cell cultured at 4° C. and then warmed to 37° C. and added into dishes. The cells were cultured with Cy5 knob-ELPs in a 37° C. incubator with 5% $CO_2$. After 10 minutes incubation, the LGACs were washed with fresh warm medium three times to remove the free Cy5-knob-S48148 in the medium. Then the cells were incubated with fresh warm medium in a 37° C. incubation chamber. The chamber is mounted on a Zeiss LSM 510 Meta confocal microscope system, which is equipped with argon and red and green He—Ne lasers and mounted on a vibration-free table.

Figure 19:
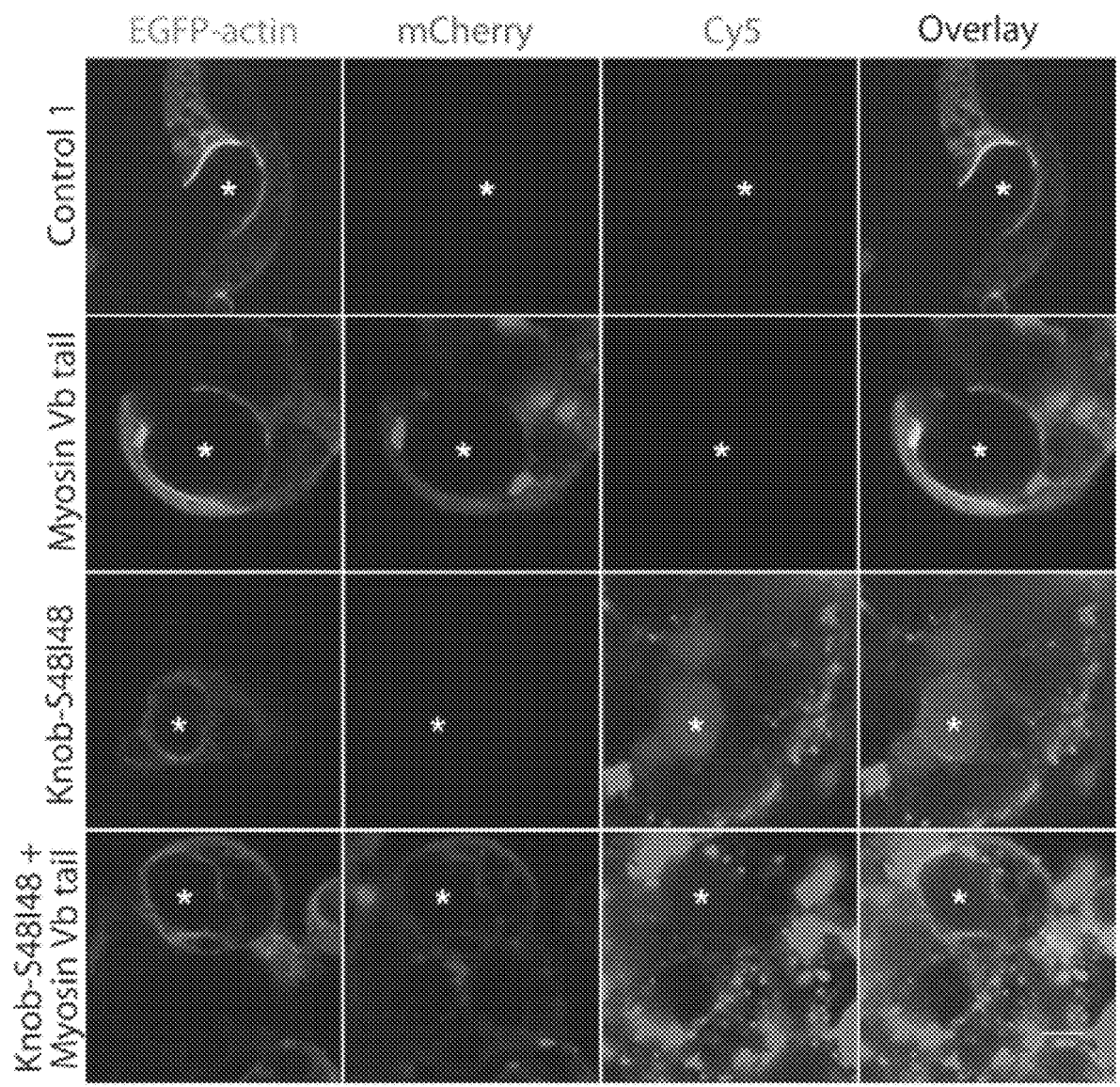
Figure 20A:
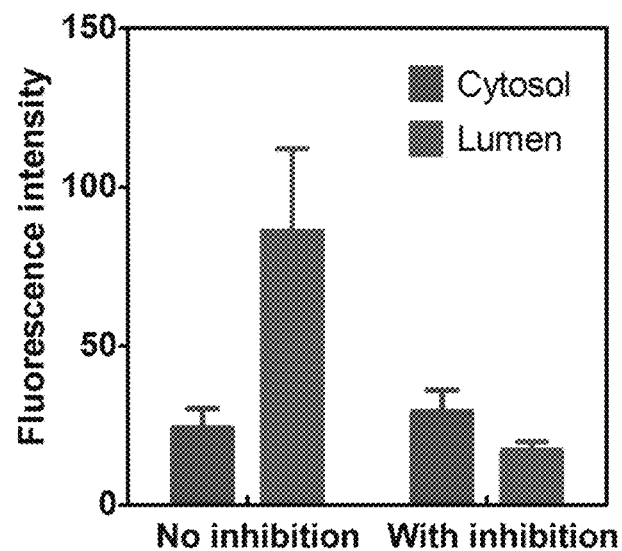
Figure 20B:
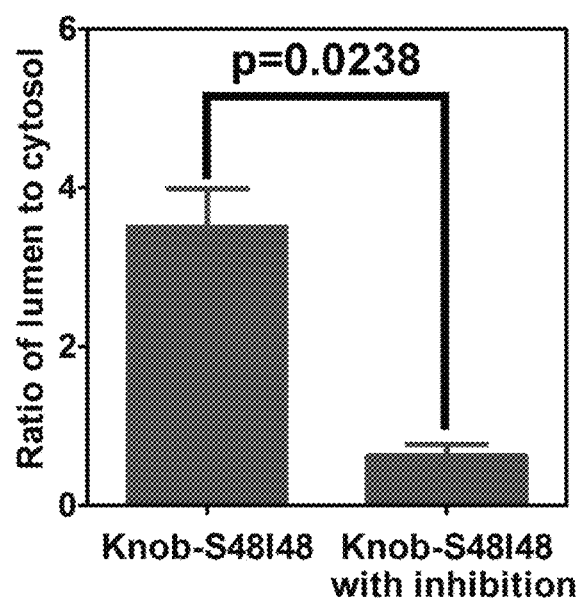

It was also found that overexpression of Myosin Vb tail suppresses accumulation of knob-S48148 nanopraticles at the acinar lumen. A mCherry myosin Vb tail, an inhibitor of LGAC transcytosis from basolateral to apical membranes, was found to significantly reduce the transcytosis of knob-S48148 (FIG. 19). Quantification of these results is shown in FIG. 20A-B. For this experiment, LGACs were pre-infected with adenovirus mCherry-Myosin Vb tail. To obtain the indication of lumen area of LGACs, the cells were also pre-infected with Adenovirus EGFP-actin and helper virus at a 37° C. incubator with 5% $CO_2$ overnight. To avoid the clash of fluorescence colours, the knob-S48148 used in transcytosis inhibition was conjugated with Cy5. The LGACs were grown on 35 mm glass-bottomed dishes for two days. Adenovirus EGFP-actin and helper virus with or without adenovirus mCherry Myosin Vb tail were added into dishes and cultured overnight. After waiting for expression of fluorescence, confocal microscopy was used to make sure adenovirus mCherry-myosin Vb tail and adenovirus EGFP-actin grow in LGACs. On the third day, knob-S48148 conjugated with Cy5 was then mixed with the cold medium at a concentration of 30 μM, warmed to 37° C. and then added into dishes. After 60 minutes incubation in a 37° C. incubator with 5% $CO_2$, LGACs were thoroughly rinsed with fresh warm medium then immediately imaged under a Zeiss LSM 510 Meta confocal microscope system, which is equipped with argon and red and green He—Ne lasers and mounted on a vibration-free table. All images were captured under the confocal microscope and processed using ImageJ (NIH, USA).

Figure 15:
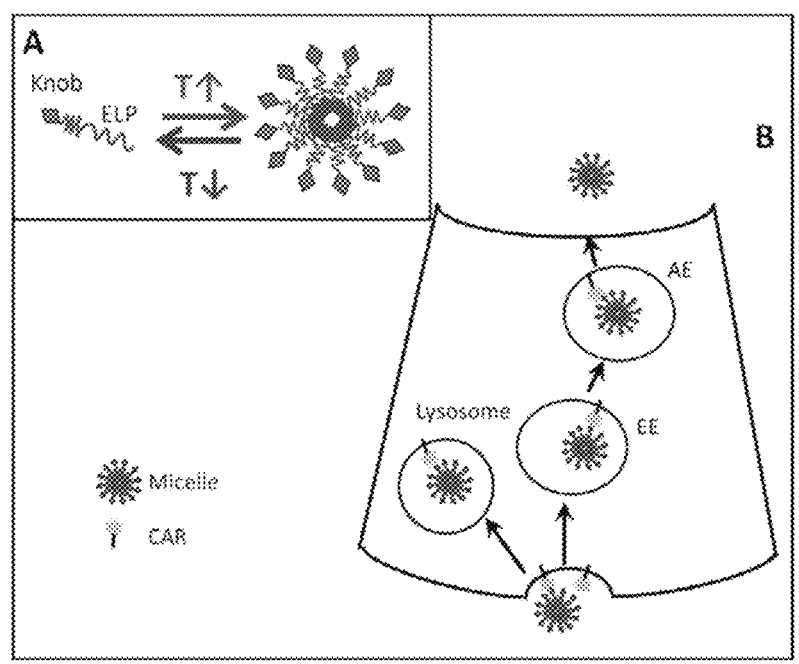
FIG. 15 is a schematic representation showing knob-S48148 nanoparticles targeted to CAR in LGACs.

FIG. 15 shows a schematic representation showing knob-S48148 nanoparticles targeted to CAR in LGACs. As depicted in FIG. 15A, Knob-S48148 reversibly assembles into micelles or disassembles into peptide monomers in response to temperature. Knob-S48148 contains a full-length Ad5 knob domain at its N-terminus followed by a thrombin cleavage site and the protein polymer S48148. FIG. 15B depicts multivalent knob-S48148 nanoparticles associate with the CAR, abundantly expressed on the cellular surface of hepatocytes and LGACs, and followed by internalization via CAR-mediated endocytosis. Endocytosed Knob-S48148 nanoparticles are transported to early endosomes in LGACs, which is followed by basal-to-apical transport to the acinar lumen, a process called transcytosis. In reconstituted rabbit LGACs, internalized knob-S48148 nanoparticles are shuttled between basal early endosomes, apical early endosomes, and sorting endosomes.

In Vivo Retention of Knob-S48148 in the LG of BALB/c Mice.

Figure 16:
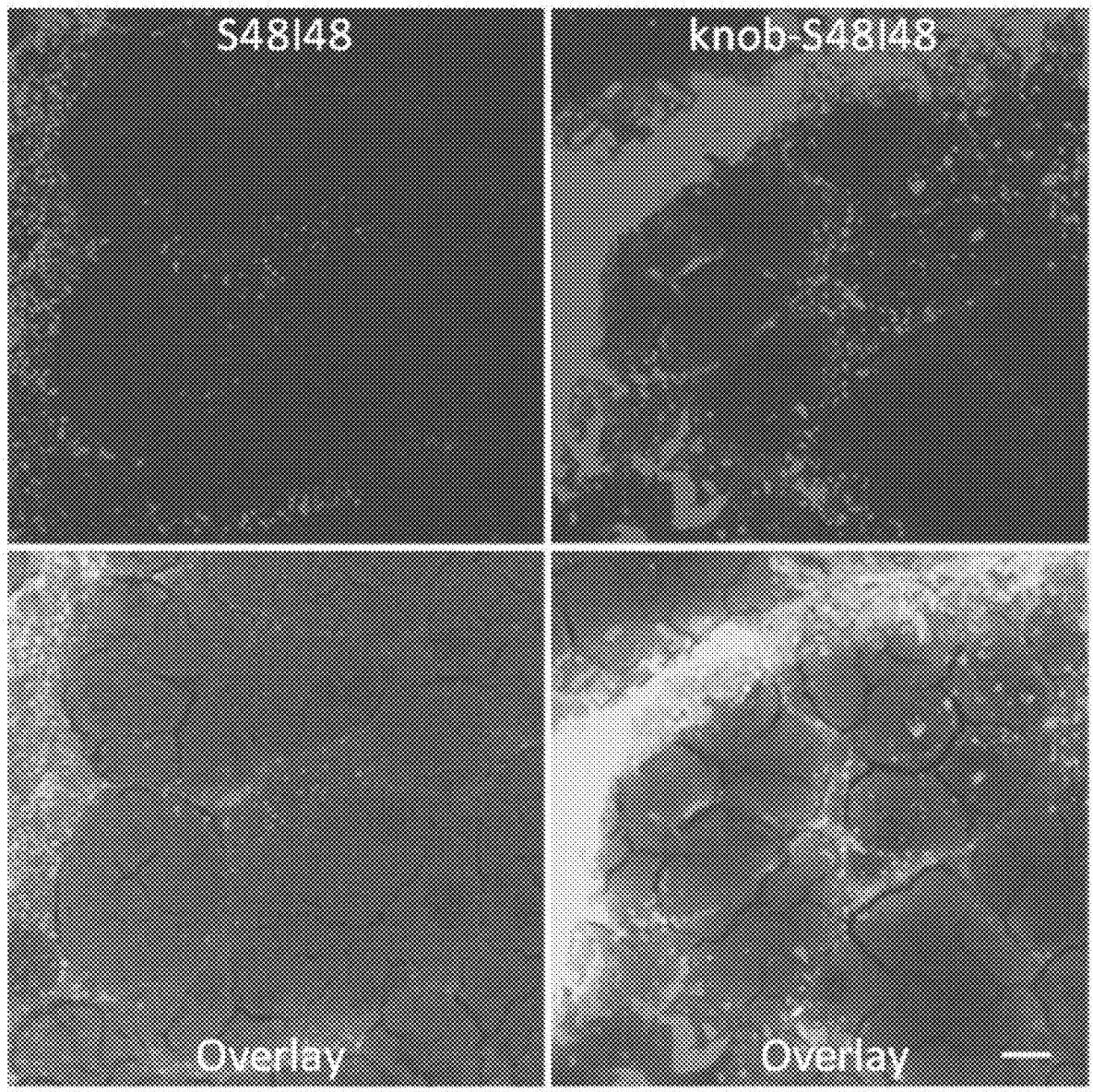
FIG. 16 shows the in vivo retention of knob-S48148 in the LG of BALB/c mice.

Twelve-week-old male BALB/c mice were administered, by intra-lacrimal gland injection, 5 μL of 50 μM rhodamine-labelled S48148 or rhodamine-labelled knob-S48148 (red) combined with 50 μg CF-dextran (10 kD, green). After 1 h, mice were euthanized and the glands were retrieved, embedded into the O.C.T. compound (Tissue-Tek), and frozen on dry ice. The frozen tissue blocks were cut into 10 μm thick sections and imaged using confocal fluorescence microscopy. The white arrows indicate endocytosed S48148 or knob-S48148 nanoparticles. The bar represents 10 μm. Mouse LGs injected with rhodamine-labelled knob-S48148 display stronger apical-membrane/luminal accumulation, surface association, and internalization than did untargeted S48148. This data is shown in FIG. 16. For this experiment, the mice were euthanatized by intraperitoneal injection with 55 mg ketamine and 14 mg xylazine per kilogram of body weight, followed by cervical dislocation. 5 μL of 50 μM rhodamine labelled knob-S48148 or S48148 was injected into the lacrimal glands of mice. After 60 minutes, the tear was collected from one eye of mouse by adding Carbachol into the related lacrimal gland. For another gland, it was removed after the tear collection was done at the first eye. After removal, LGs were snap frozen and stored on the dry ice. The frozen glands were cut into 10 μm thick sections and mounted on glass slides. Then the sections were examined with a confocal laser scanning microscope (LSM) at excitation wavelengths of 488 and 534 nm.

Knob-ELP Purification

Figure 2:
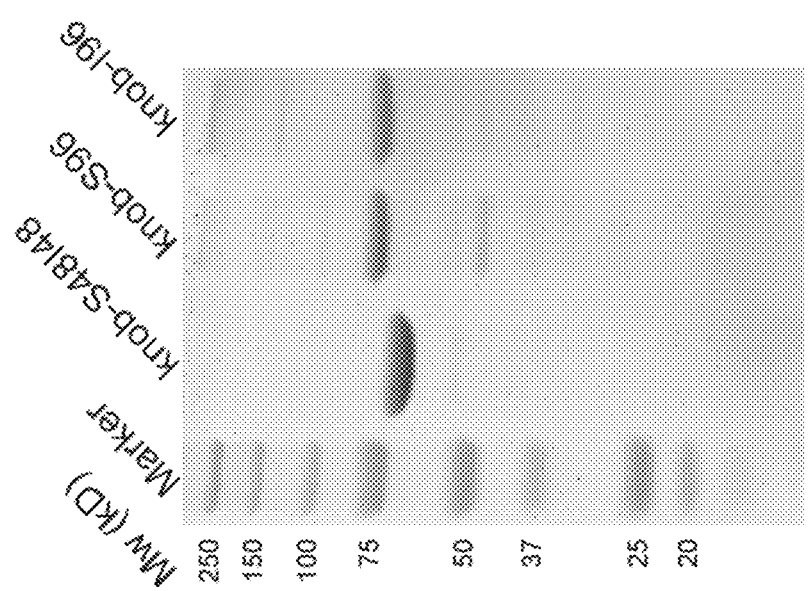
FIG. 2 shows denaturing SDS-PAGE for knob-ELPs. The knob-I96, knob-S96 and knob-S48I48 were purified by inverse phase transition cycling (ITC) and resolved by SDS-PAGE stained with Coomassie brilliant blue. The molecular weights of marker proteins lane are 250, 150, 100, 75, 50, 37, 25 and 20 kD, as listed.

A series of ELPs were genetically engineered, expressed in *E. coli*, and purified using the ELP temperature-dependent phase transition property (Table 1). The purified material was characterized for molecular weight and purity using SDS-PAGE and matrix assisted laser desorption ion mass spectrometry (FIG. 2, Table 1). Three fusion peptides with knob were prepared, knob-S96, knob-S48148, and knob-I96. The ELPs S96 and I96 have a high and low transition temperature respectively; however, they do not form nanoparticles (data not shown). In contrast, the ELP S48148 was shown to form nanoparticles at physiological temperatures (Table 1). Each of these fusion peptides appears as a major band around 60 kD (FIG. 2), which corresponds to the predicted and observed molecular weights as determined using mass spectrometry (Table 1). Some contaminating *E. coli* proteins appear to co-purify with both knob-I96 and knob-S96 but not knob-S48148. Although not essential for this study, the non-chromatographic purification of proteins fused to ELPs represents a powerful advantage of this approach.

Characterization of Knob-ELP

Figure 3:
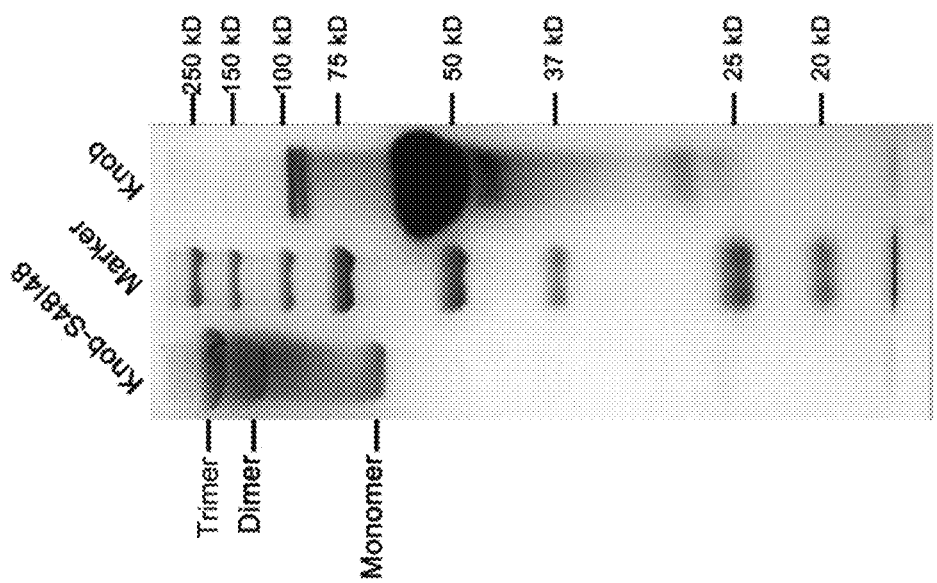
FIG. 3 shows non-denatured-PAGE of knob-S48I48. The knob-S48I48 was mixed with non-denaturing sample buffer (without 2-mercapto-ethanol) and resolved by PAGE. The gel was then stained with Coomassie brilliant blue. The molecular weights of the marker lanes are 250, 150, 100, 75, 50, 37, 25 and 20 kD (from top to bottom), respectively.

To determine if the knob-ELP fusion peptides exist in a trimeric form, as they do for native adenovirus as required for appropriate CAR binding, non-denaturing gel electrophoresis was performed (FIG. 3). Knob-S48148 surprisingly showed three strong bands around 60 kD, 120 kD and 180 kD, which indicated monomer, dimer and trimer forms of knob-ELP. For comparison, a recombinant knob purified using nickel affinity chromatography (without ELP) was also confirmed to form predominantly trimers. The recombinant knob lane indicates several minor bands, with molecular weights slightly lower than knob. These minor bands may come from partial proteolysis of knob. This data suggests that the ELP architecture may influence the native quaternary structure of fused proteins domains, whereby block copolymers that assemble nanoparticles (S48148) also promote formation of native trimers. So the recombinant knob-ELP has properties similar to those of the native knob.

To characterize the ELP behavior of the knob fusion peptides, the transition temperatures were identified by optical density (FIG. 4) and the assembly of nanoparticles was confirmed using dynamic light scattering. Knob-S96, a monoblock ELP, only exhibits one increase in optical density over a temperature gradient at a temperature well above physiological conditions. Knob-I96 also shows a single increase in optical density; however, due to the hydrophobicity of the isoleucine X residue, this fusion peptide phase-separates near room temperature. In contrast, the diblock ELP Knob-S48148 displayed two phase transition temperatures, one around 19.5° C. and another around 60° C. Qualitatively, this behavior is similar to S48148, which has two transition temperatures at 26.5 and 75° C. For knob-S48148, at temperatures below 19.5° C., the polypeptides are free in solution; however, between 19.5 and about 40° C. the peptides are presumed to form nanoparticles. Above 60° C., the S48 block phase separates, and nanoparticles are not stable. By comparing the critical aggregation temperatures of knob-S48148 and S48148, it can be easily observed that the knob domain slightly depresses the nanoparticle assembly temperature (Table 1).

Figure 4:
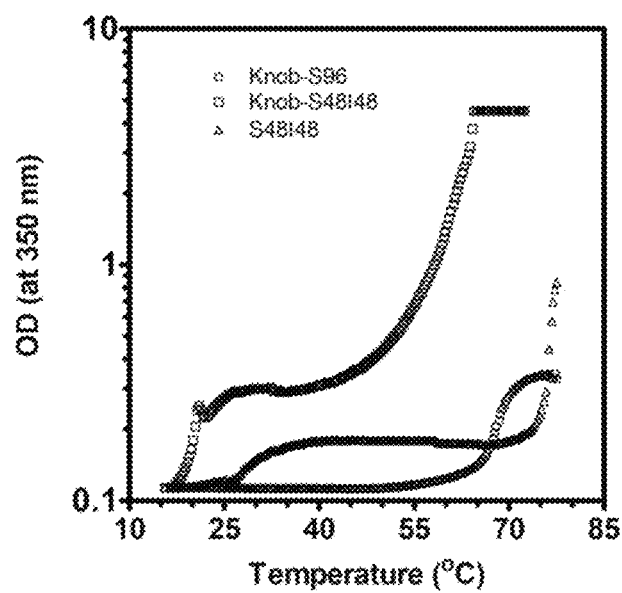
FIG. 4 shows temperature-dependence of the optical density for ELP fusion peptides. Phase transition behavior of knob-S96, S48I48 and knob-S48I48. Each sample was diluted to 25 M in PBS at 4° C. The OD of samples at 350 nm was measured using a spectrophotometer with increasing temperatures from 15 to 80° C.
Figure 5A:
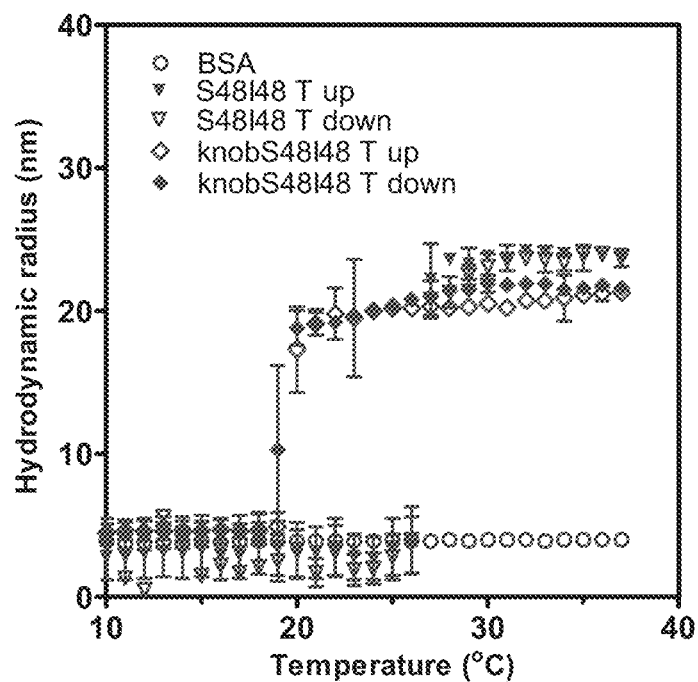
FIGS. 5A-5B show the temperature-dependent assembly and disassembly for ELP fusion peptides. Dynamic light scattering was used to characterize S48I48 and knob-S48I48. (A) S48I48 and knob-S48I48 were diluted at 25 μM in PBS and passed through a 20 nm filter at 4° C. before measurement in a DynaPro plate reader. Readings were taken starting with an increase from 10° C. to 37° C. and then a decrease from 37° C. to 10° C. BSA was only measured from 10° C. to 37° C. (B) Statistical comparison for nanoparticles radius for BSA, S48I48 and knob-S48I48 at 15° C. and 37° C. *** indicates p<0.01 as determined using the Tukey post-hoc test.
Figure 5B:
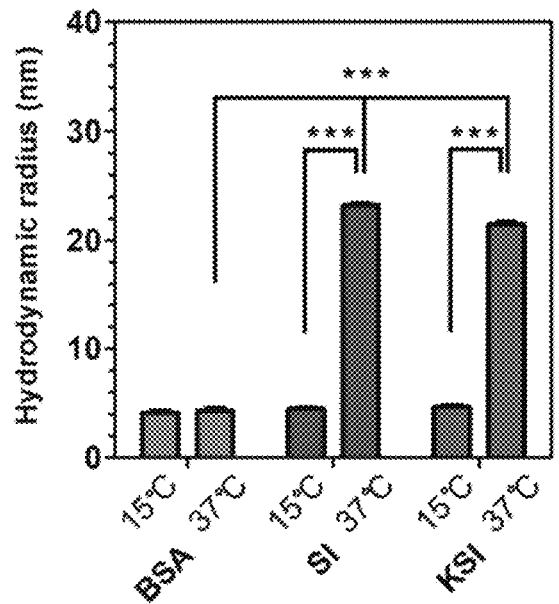

While optical density is useful to determine the temperature of assembly, dynamic light scattering is necessary to verify the size and formation of stable nanoparticles. Upon heating, both S48148 and knob-S48148 self-assemble into nanoparticles and this assembly was shown to be reversible upon cooling (FIG. 5(A)). When the temperature increased from 10 to 37° C., both knob-S48148 and S48148 transitioned from unimers to nanoparticles, of a radius previously shown to be nanoparticles (see, for e.g., M. R. Dreher, et. al. J Am Chem Soc 130(2) (2008) 687-694). This assembly is reversible, and the nanoparticles were disassembled into unimers when temperature decreased from 37 to 10° C. It was shown by DLS that S48148 and knob-S48148 self-assemble into nanoparticles with a diameter consistent with micelles as reported (see, for e.g., M. R. Dreher, et. al. J Am Chem Soc 130(2) (2008) 687-694). At physiological temperature (37° C.), the hydrodynamic radii of S48148 and knob-S48148 nanoparticles were 23.7 and 21.7 nm respectively. As observed using dynamic light scattering, the critical nanoparticle temperature (CNT) for knob-ELP is 19.5° C. while ELP without knob is 26.5° C. This downward shift in CNT is consistent with that observed by optical density (FIG. 4). While the addition of knob to the ELP lowers the nanoparticle assembly temperature, it did not change the hydrodynamic radius. The control BSA exhibits a stable size around 4 nm, the same as the unimers of knob-S48148 and S48148, because BSA does not have any phase transition behavior. The ANOVA results (FIG. 5(B)) indicate that BSA, S48148 and knob-S48148 have similar sizes at 15° C., while the particles size of S48148 and knob-S48148 had a significantly larger radii at 37° C. compared with BSA ($p<0.01$).

Figure 18A:
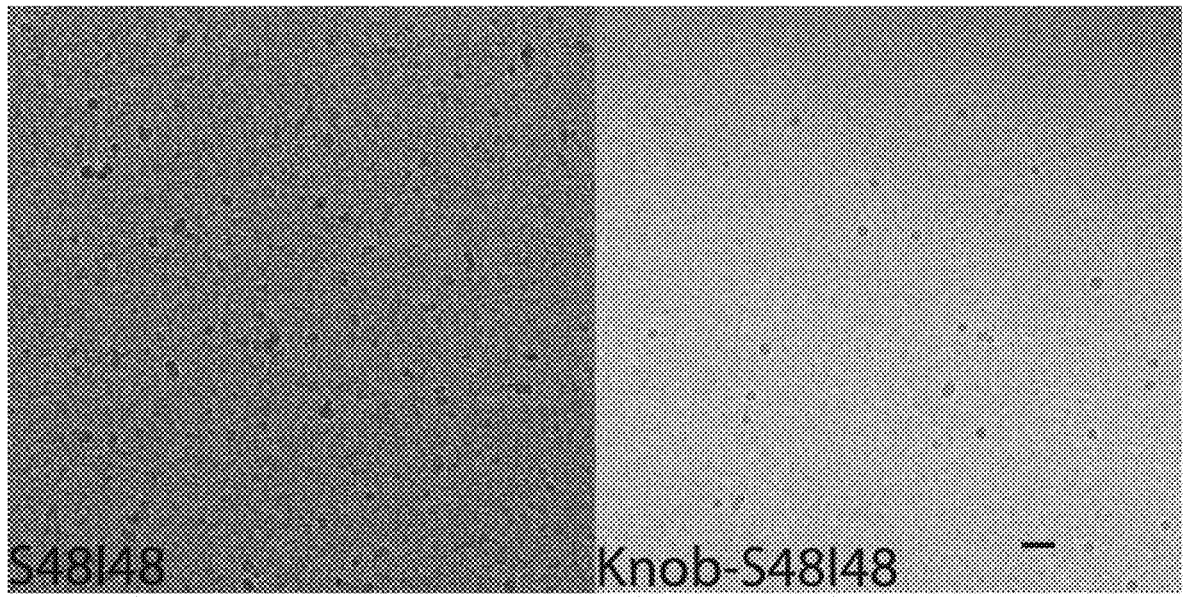
FIGS. 18A-18B show the spherical morphology of S48148 protein polymer nanoparticles with and without the Knob domain.
Figure 18B:
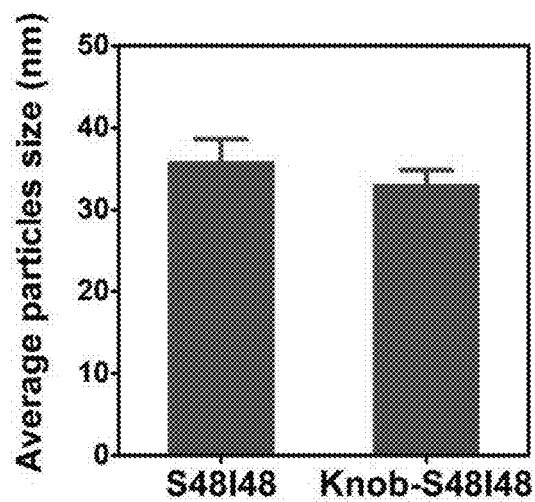

S48148 protein polymer nanoparticles with and without the Knob domain were viewed by cryo-transmission electron microscopy (TEM) imaging. Cryo-TEM specimens were prepared using FEI Vitrobot (Hillsboro, Oreg.). ELP solutions were kept in an ice bath (4° C.) before processing. A typical procedure involves first loading ~6 uL of the sample on a TEM grid coated with a lacey carbon film (LC325-Cu, Electron Microscopy Sciences). Then, the specimen was carefully blotted under 95% humidity following blotting parameters that were preset depending on the viscosity and concentration of the studied sample. The blotted grid was immediately transferred into liquid ethane, and stored in liquid nitrogen environment. Micrographs were acquired using FEI Tecnai 12 TWIN transmission electron microscope equipped with 16 bit 2K×2K FEI eagle bottom mount camera (Hillsboro, Oreg.). All images were captured under 100 kV accelerating voltage and processed using ImageJ (NIH, USA). As shown in FIG. 18B, the particles were found to have an average particle size from about 30-40 nm.

Cleavage of Knob-ELP

Figure 6:
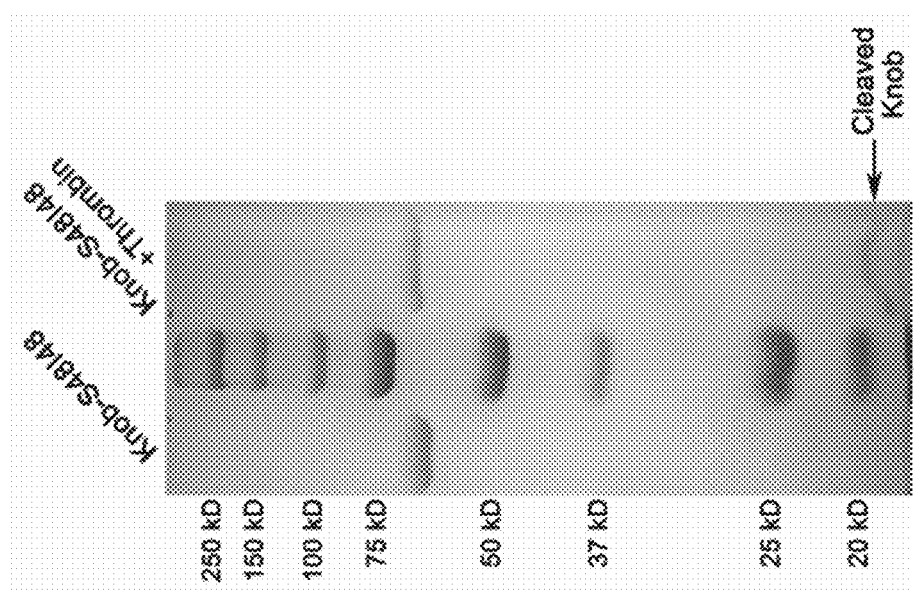
FIG. 6 shows proteolytic release of knob from knob-ELP. Left lane is knob-S48I48 before cleavage and right lane is knob-S48I48 after incubation with thrombin overnight at room temperature. The gel was stained by Coomassie brilliant blue. The position of the cleaved knob domain near 20 kD is shown in the right lane.

To determine if these ELPs can be utilized as a strategy to purify free knob, a thrombin recognition site was incorporated into the construct between knob and the ELP (Table 1). The knob-S48148 construct was incubated with a thrombin cleavage solution, which partially cleaved the fusion peptide, as validated by a band near 20 kD (FIG. 6). Since the thrombin recognition site can be cleaved, there exists the possibility of harvesting recombinant knob from knob-ELP fusion peptides. More importantly, the molecular weight bands resulting from cleavage of knob from ELP further confirm the successful expression of the knob-ELP constructs.

Cellular Uptake

Figure 7:
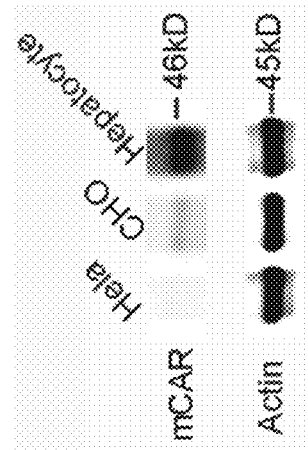
FIG. 7 shows murine hepatocytes expresses coxsackie adenovirus receptor (CAR). Hepatocytes, CHO, and Hela cells were lysed with SDS-PAGE sample buffer and CAR expression detected with western blot via primary goat anti mouse CAR and mouse anti-actin antibodies, as well as the secondary goat anti-mouse antibodies sold under IRDYE® 800 donkey anti-goat and IRDYE® 700 goat anti-mouse antibodies.

To determine if knob-mediated internalization is conferred to knob-ELP fusion peptides, live cell uptake experiments were conducted to study the internalization of knob-S48148 into a hepatocyte cell line. This study was carried out in transformed mouse hepatocytes because of the high expression of CAR, which has been hypothesized to mediate the novel fiber and knob-dependent endocytotic uptake that has been observed. Prior to uptake studies, it was necessary to confirm that the hepatocyte cell line does express CAR (FIG. 7). A western blot comparing CAR expression in three representative and commonly utilized cell types indicated that hepatocyte lysates showed very strong immunoreactivity around 46 kD in mouse hepatocyte cell lysate only, which is the correct molecular weight for CAR. CHO cell lysates showed a slight band and there was no expression detectable in Hela cell lysates.

Figure 8:
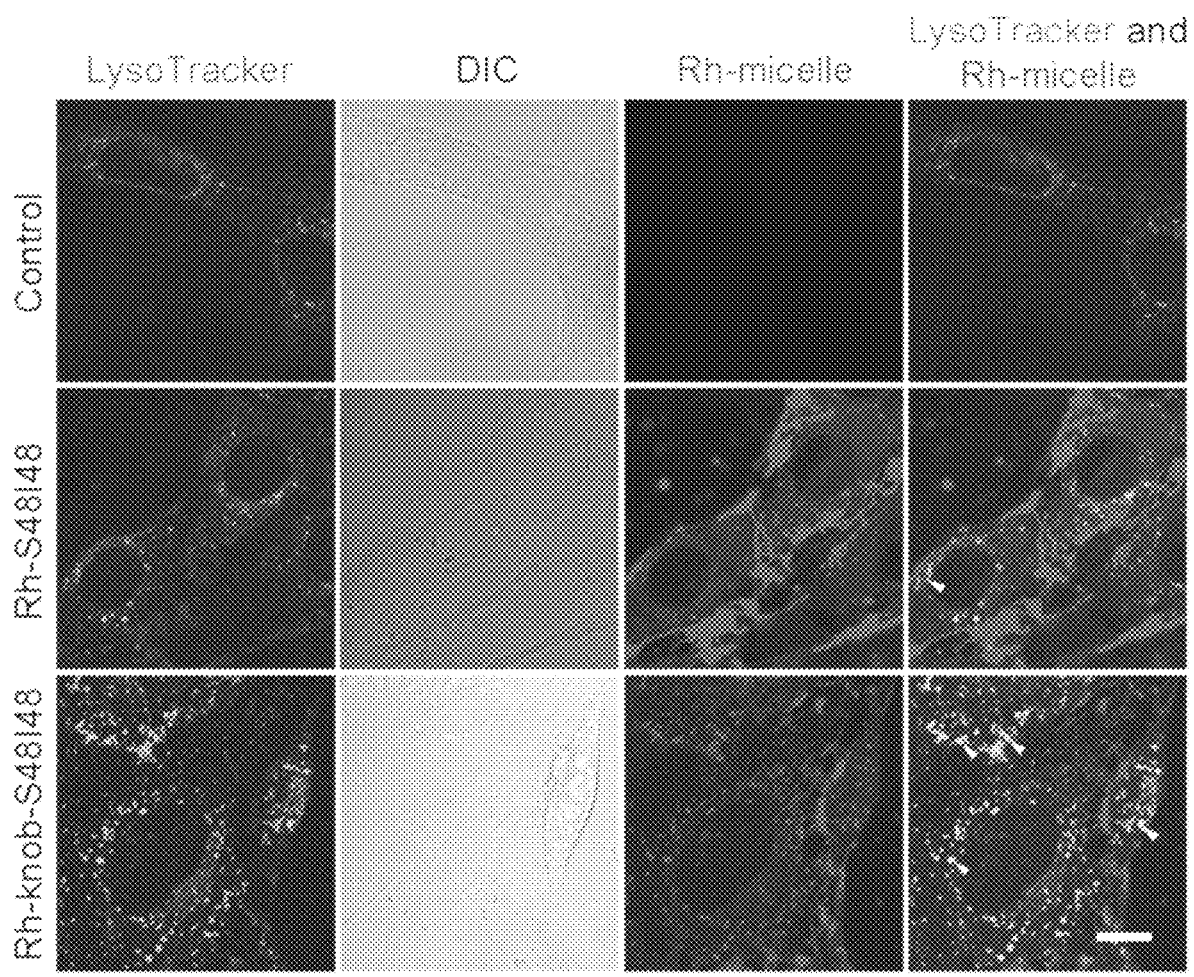
FIG. 8 demonstrates live cell imaging of cellular uptake for ELP and knob-ELP nanoparticles. Transformed mouse hepatocytes grown on 35 mm glass-bottomed dishes were incubated in medium containing 10 μM rhodamine-conjugated S48I48 or knob-S48I48 (red) with 75 nM LYSOTRACKER® green (green) at 37° C. for 30 minutes and imaged using confocal microscopy. Knob-S48I48 exhibited markedly more co-localization with LYSOTRACKER® green while S48I48 exhibited more apparent surface association. The arrows indicated the internalized nanoparticles co-localized with lysosome. Scale bar: 10 μm.

Having demonstrated that the hepatocyte cell line expresses CAR, a rhodamine-labeled knob-S48148 was employed to explore uptake via the CAR pathway. A rhodamine-labeled S48148 was used as a control for cell-surface binding of ELPs. With 30 minutes incubation at 37° C., there was a significant cellular uptake of knob-S48148 (FIG. 8). For reference, LYSOTRACKER® green was used to stain low pH lysosomes inside the cells. A control sample without ELP shows no signal (absence of red labeling). In contrast, both knob-S48148 and S48148 can be clearly seen at the surface of the hepatocytes. Compared with S48148, knob-S48148 exhibited much stronger punctate red fluorescence inside hepatocyte cells, and S48148 exhibited slightly more intense fluorescence on the cell surface. Both the intracellular fluorescence of knob-S48148 and S48148 that was seen was co-localized with low pH compartments; however, only knob-S48148 showed an abundant punctate intracellular fluorescence labeling pattern (FIG. 8).

Figure 9:
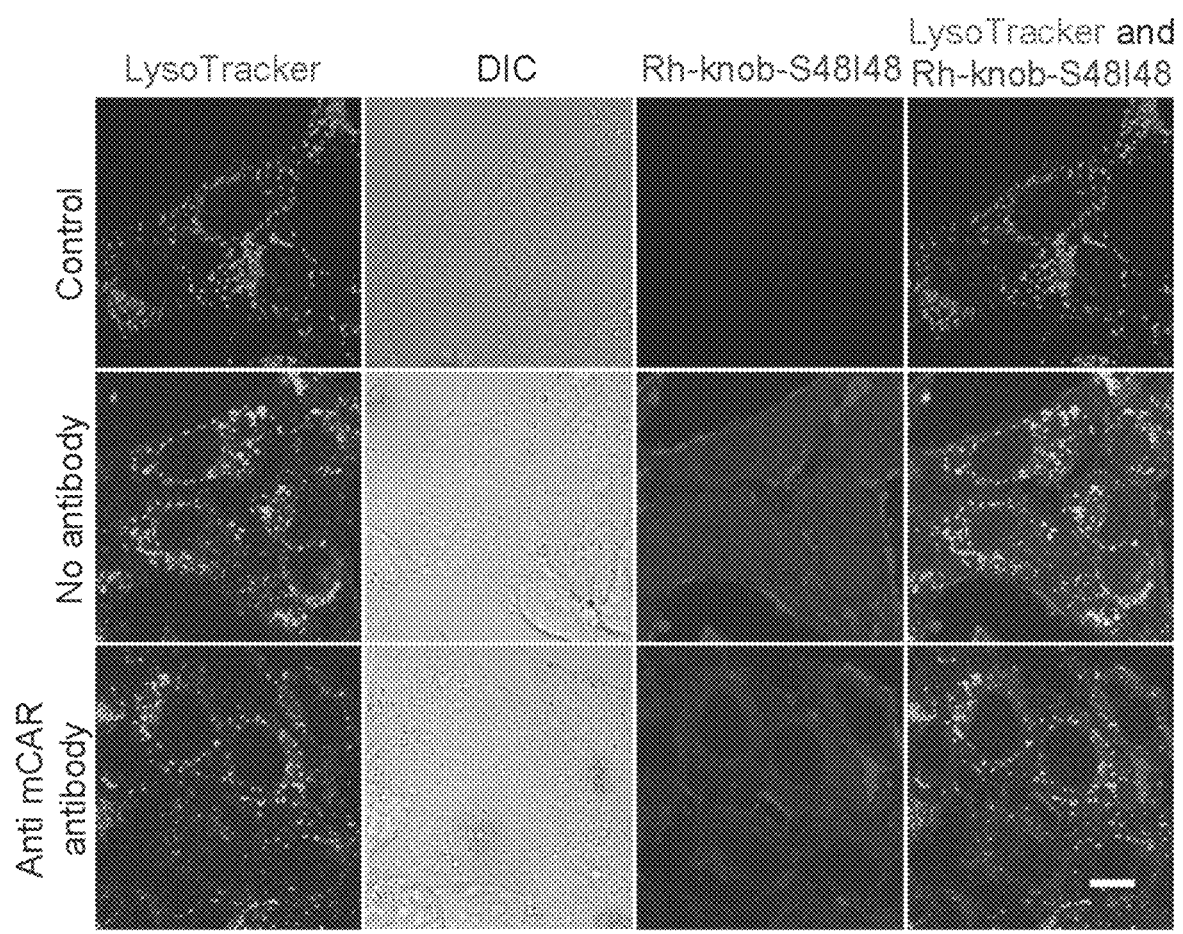
FIG. 9 shows competitive binding and uptake of knob-S48I48 with anti-mouse CAR antibody. Live cell imaging was performed on transformed mouse hepatocytes grown on 35 mm glass-bottomed dishes were pre-incubated with 20 μg/mL anti-mouse CAR antibody at 37° C. for 30 minutes. Rhodamine-conjugated knob-S48I48 (red, 10 μM) with the green dye sold under LYSOTRACKER® green was added into the medium. After 30 minutes the cells were rinsed with fresh warm medium and imaged using confocal microscopy. Scale bar: 10 μm.
Figure 10:
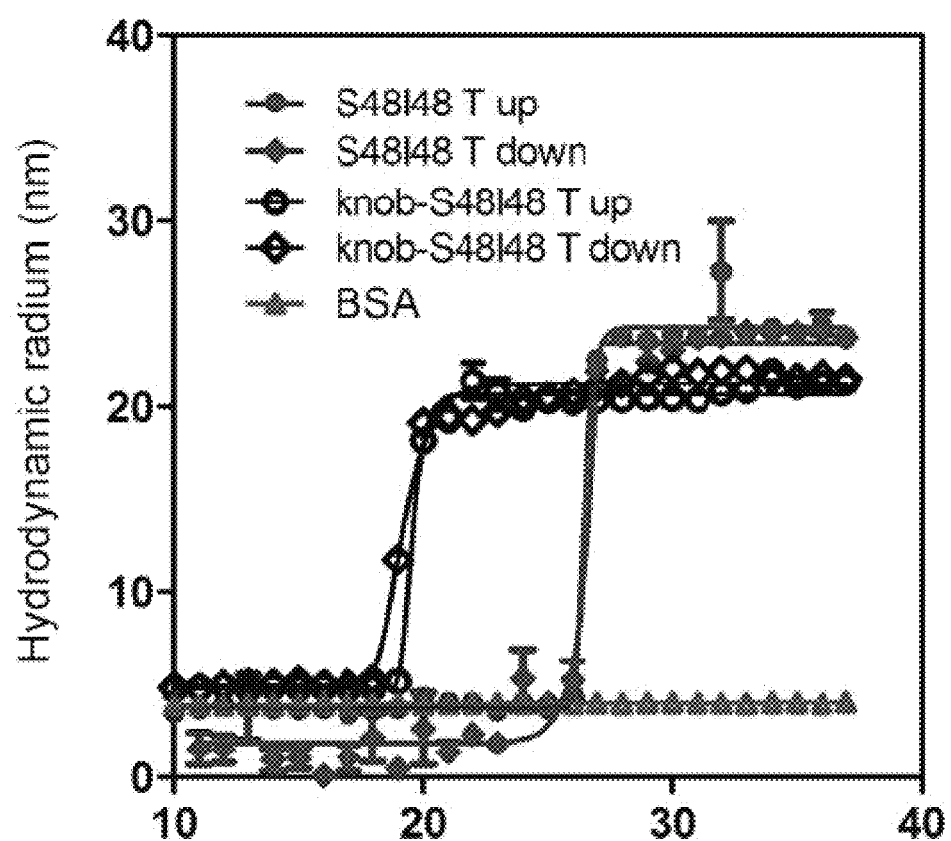
FIG. 10 shows self-assembly or disassembly of nanoparticles above or below their phase transition temperatures. S48I48 and Knob-S48I48 were passed through a 20 nm microfilter at 4° C. in PBS and characterized by dynamic light scattering spectroscopy (DynaPro plate reader). Readings were taken starting with an increase from 10° C. to 37° C. and then decrease from 37° C. to 10° C. BSA was only measured from 10° C. to 37° C.
Figure 11:
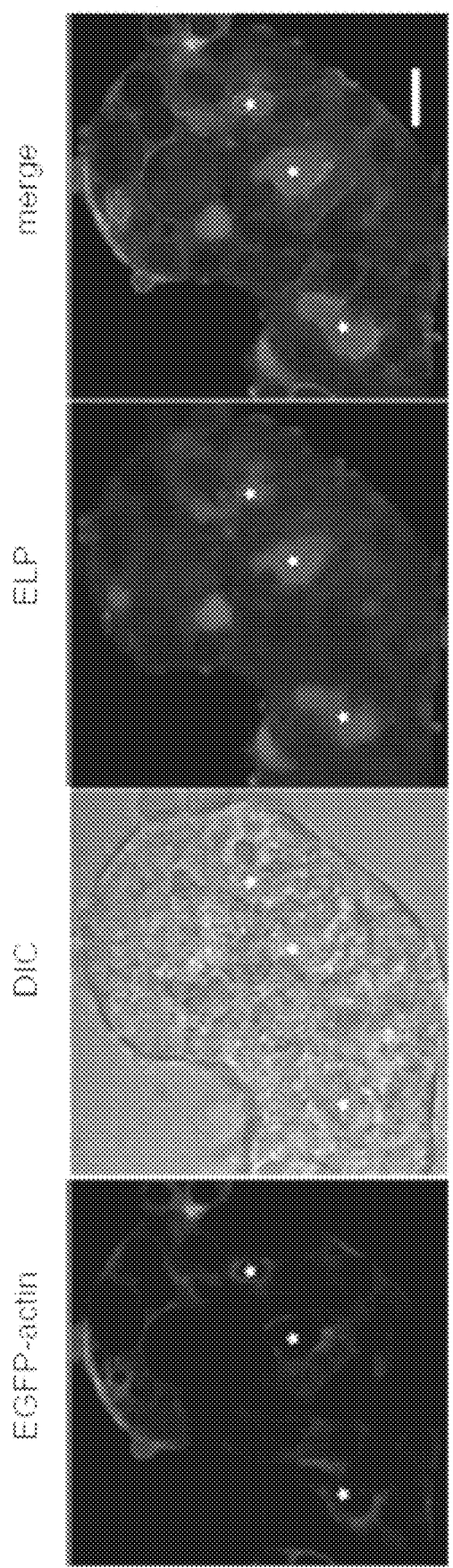
FIG. 11 shows knob-ELP nanoparticles transcytosed in LGACs. Scale bar represents 10 m.
Figure 12:
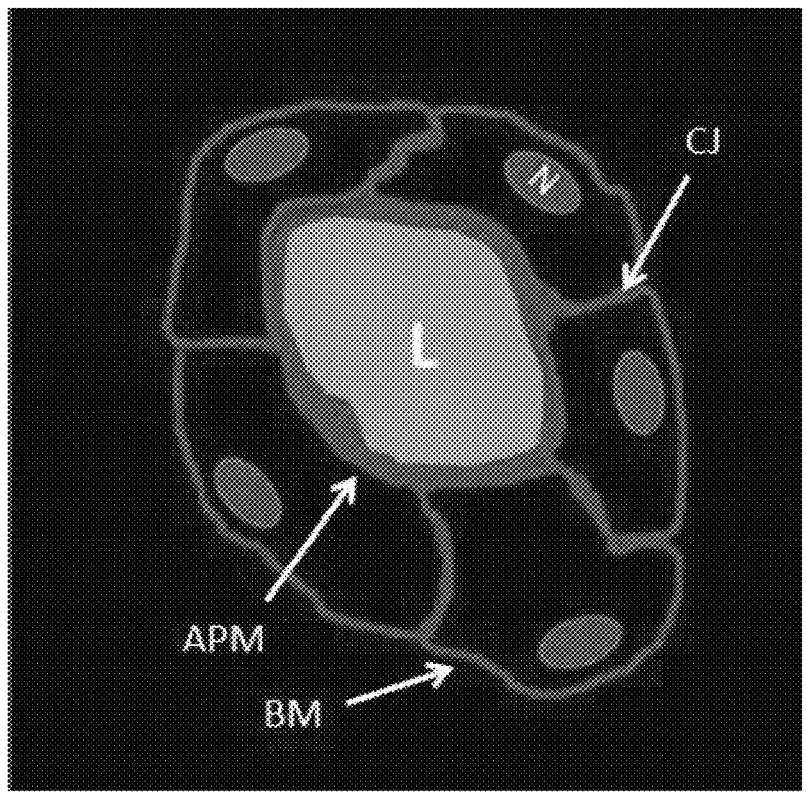
FIG. 12 shows a schematic representation of reconstituted LG acinar cluster. L represents acinar lumena. N represents cell nucleus. APM represents apical membrane. BM represents basal-lateral membrane. CJ represents cell junction.

Having demonstrated an effect of the fused knob domain on the cellular internalization of the fluorescent label, a competitive binding study was used to determine the specificity of uptake for the CAR pathway (FIG. 9). Pre-incubation with anti-mouse CAR antibody reduced the intracellular punctate fluorescence associated with intracellular knob-S48148 nanoparticles relative to the signal detected in hepatocytes without antibody pre-binding. This result suggests the anti-mouse CAR antibody blocks or alters the internalization of knob-S48148 into hepatocytes. Incubation with a non-specific antibody similarly did not affect knob-S48148 uptake (data not shown). In conjunction with the previous experiment, this data supports a model of uptake of knob-ELP nanoparticles via a unique CAR-mediated endocytotic pathway.

To develop a novel targeted drug carrier, the knob domain of fiber protein from adenovirus 5 was fused with a diblock ELP capable of assembling nanoparticles. Plasmids encoding knob-ELP and ELP were constructed and purified from *E. coli*. Non-denaturing PAGE demonstrated that knob-ELP fusion peptides form trimeric and dimeric quaternary structures, which is a property of the native knob. Dynamic light scattering indicated that both knob-S48148 and S48148 can self-assemble into compact nanoparticles, with hydrodynamic diameters around 40 nm. The critical nanoparticle temperature of S48148 and knob-S48148 were 26.5 and 19.5° C. respectively. Cellular uptake experiments indicated that both S48148 and knob-S48148 bind a hepatocyte cell line; however, the knob-S48148 showed more intracellular vesicular uptake, specifically into lysosomal compartments. A competitive binding experiment with anti mouse CAR antibody blocks the internalization of knob-S48148, suggesting that uptake is mediated by knob-CAR binding and endocytosis. Unlike adenovirus, this simplified fusion peptide lacks many of the capsid proteins responsible for immunogenicity; furthermore, the knob-domain lacks the adenoviral RGD motif that targets integrins. As such, these polypeptide nanoparticles are a potentially useful new class of drug carriers that target a unique uptake mechanism, which is differentially expressed throughout the body.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention such as for example, embodiments described in Appendix A attached hereto. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A drug delivery agent comprising an elastin-like peptide (ELP) component, a ligand component, and an anticancer drug, wherein the ELP component comprises the polypeptide of SEQ ID NO: 1, and wherein the ligand component is a knob ligand comprising the polypeptide of SEQ ID NO: 4.

2. The drug delivery agent of claim 1, wherein the ELP component comprises a diblock.

3. The drug delivery agent of claim 1, wherein the ELP component comprises the polypeptide of SEQ ID NO: 12, or SEQ ID NO: 13, or SEQ ID NO: 14.

4. The drug delivery agent of claim 1, wherein the ELP component comprises the polypeptide of SEQ ID NO: 12.

5. A method for delivering a drug comprising an elastin-like peptide (ELP) to a cell, comprising contacting the cell with the drug delivery agent of claim 1.

6. The method of claim 5, wherein the cell is one or more of a mucosal cell, an epithelial cell or a hepatocyte.

7. The method of claim 5, wherein the cell is contained within a lacrimal gland or tissue.

8. A method for delivering a drug to the luminal area of lacrimal gland acinar cells (LGACs) by transcytosis, comprising contacting the LGACs with the drug delivery agent of claim 1.

9. The method of claim 8, wherein the drug is in contact with the ocular surface of the eye.

10. The method of claim 8, wherein the drug is released from interstitial to luminal surfaces on a mucosal epithelial cell.

11. A method for treating a disease of the lacrimal gland, comprising administering to a patient in need of such treatment the drug delivery agent of claim 1, thereby treating the patient.

12. The method of claim 11, wherein the disease is cancer or Sjorgren's Syndrome.

13. A drug delivery agent comprising an elastin-like peptide (ELP) component, a ligand component, and an anticancer drug, wherein the ELP component comprises the polypeptide of SEQ ID NO: 12, or SEQ ID NO: 13, or SEQ ID NO: 14, and wherein the ligand component is a knob ligand comprising the polypeptide of SEQ ID NO.

14. The drug delivery agent of claim 13, wherein the ELP component comprises the polypeptide of SEQ ID NO: 12.

15. A method for delivering a drug comprising an elastin-like peptide (ELP) to a cell, comprising contacting the cell with the drug delivery agent of claim 13.

16. A method for delivering a drug to the luminal area of LGACs by transcytosis, comprising contacting the LGAC with the drug delivery agent of claim 13.

17. A method for treating a disease of the lacrimal gland, comprising administering to a patient in need of such treatment the drug delivery agent of claim 13, thereby treating the patient.

* * * * *

UNITED STATES PATENT AND TRADEMARK OFFICE
CERTIFICATE OF CORRECTION

| | |
|---|---|
| PATENT NO. | : 11,224,662 B2 |
| APPLICATION NO. | : 16/230698 |
| DATED | : January 18, 2022 |
| INVENTOR(S) | : Hamm-Alvarez et al. |

Page 1 of 1

It is certified that error appears in the above-identified patent and that said Letters Patent is hereby corrected as shown below:

In the Specification

In Column 1, Lines 18-23, please delete "The presently disclosed subject matter was made with United States Government support under Grant Nos. EY017293-S1, EY017293 and 5-P30-CA14089, awarded by the National Institutes of Health (NIH). The United States Government has certain rights in the presently disclosed subject matter." and insert -- This invention was made with government support under EY017293 and 5-P30-CA14089 awarded by the National Institutes of Health (NIH). The government has certain rights in the invention." --

Signed and Sealed this
Twelfth Day of April, 2022

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 1

Val Pro Gly Xaa Gly
1               5

<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 2

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
            20                  25                  30

Gly Ser Gly Val Pro Gly Ser Gly Val Pro Gly Ser Gly Val Pro Gly
        35                  40                  45

Ser Gly Val Pro Gly Ser Gly Val Pro Gly Ser Gly Val Pro Gly Ser
    50                  55                  60

Gly Val Pro Gly Ser Gly Val Pro Gly Ser Gly Val Pro Gly Ser Gly
65                  70                  75                  80

Val Pro Gly Ser Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125

Ser Gly Val Pro Gly Ser Gly Val Pro Gly Ser Gly Val Pro Gly Ser
    130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
                165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
        195                 200                 205

Ser Gly Val Pro Gly Ser Gly Val Pro Gly Ser Gly Val Pro Gly Ser
    210                 215                 220

Gly Val Pro Gly Ser Gly Val Pro Gly Ser Gly Val Pro Gly Ser Gly
225                 230                 235                 240

<210> SEQ ID NO 3
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Pro Gly Ile Gly Val Pro Gly Ile Gly Val Pro Gly Ile Gly Val
1               5                   10                  15

Pro Gly Ile Gly Val Pro Gly Ile Gly Val Pro Gly Ile Gly Val Pro
            20                  25                  30

Gly Ile Gly Val Pro Gly Ile Gly Val Pro Gly Ile Gly Val Pro Gly
        35                  40                  45

Ile Gly Val Pro Gly Ile Gly Val Pro Gly Ile Gly Val Pro Gly Ile
    50                  55                  60

Gly Val Pro Gly Ile Gly Val Pro Gly Ile Gly Val Pro Gly Ile Gly
65                  70                  75                  80

Val Pro Gly Ile Gly Val Pro Gly Ile Gly Val Pro Gly Ile Gly Val
                85                  90                  95

Pro Gly Ile Gly Val Pro Gly Ile Gly Val Pro Gly Ile Gly Val Pro

```
                    100                 105                 110
Gly Ile Gly Val Pro Gly Ile Gly Val Pro Gly Ile Gly Val Pro Gly
                115                 120                 125
Ile Gly Val Pro Gly Ile Gly Val Pro Gly Ile Gly Val Pro Gly Ile
                130                 135                 140
Gly Val Pro Gly Ile Gly Val Pro Gly Ile Gly Val Pro Gly Ile Gly
145                 150                 155                 160
Val Pro Gly Ile Gly Val Pro Gly Ile Gly Val Pro Gly Ile Gly Val
                165                 170                 175
Pro Gly Ile Gly Val Pro Gly Ile Gly Val Pro Gly Ile Gly Val Pro
                180                 185                 190
Gly Ile Gly Val Pro Gly Ile Gly Val Pro Gly Ile Gly Val Pro Gly
                195                 200                 205
Ile Gly Val Pro Gly Ile Gly Val Pro Gly Ile Gly Val Pro Gly Ile
                210                 215                 220
Gly Val Pro Gly Ile Gly Val Pro Gly Ile Gly Val Pro Gly Ile Gly
225                 230                 235                 240

<210> SEQ ID NO 4
<211> LENGTH: 195
<212> TYPE: PRT
<213> ORGANISM: Human adenovirus

<400> SEQUENCE: 4

Gly Ala Ile Thr Val Gly Asn Lys Asn Asn Asp Lys Leu Thr Leu Trp
1               5                   10                  15
Thr Thr Pro Ala Pro Ser Pro Asn Cys Arg Leu Asn Ala Glu Lys Asp
                20                  25                  30
Ala Lys Leu Thr Leu Val Leu Thr Lys Cys Gly Ser Gln Ile Leu Ala
            35                  40                  45
Thr Val Ser Val Leu Ala Val Lys Gly Ser Leu Ala Pro Ile Ser Gly
        50                  55                  60
Thr Val Gln Ser Ala His Leu Ile Ile Arg Phe Asp Glu Asn Gly Val
65                  70                  75                  80
Leu Leu Asn Asn Ser Phe Leu Asp Pro Glu Tyr Trp Asn Phe Arg Asn
                85                  90                  95
Gly Asp Leu Thr Glu Gly Thr Ala Tyr Thr Asn Ala Val Gly Phe Met
                100                 105                 110
Pro Asn Leu Ser Ala Tyr Pro Lys Ser His Gly Lys Thr Ala Lys Ser
                115                 120                 125
Asn Ile Val Ser Gln Val Tyr Leu Asn Gly Asp Lys Thr Lys Pro Val
            130                 135                 140
Thr Leu Thr Ile Thr Leu Asn Gly Thr Gln Glu Thr Gly Asp Thr Thr
145                 150                 155                 160
Pro Ser Ala Tyr Ser Met Ser Phe Ser Trp Asp Trp Ser Gly His Asn
                165                 170                 175
Tyr Ile Asn Glu Ile Phe Ala Thr Ser Ser Tyr Thr Phe Ser Tyr Ile
                180                 185                 190
Ala Gln Glu
        195

<210> SEQ ID NO 5
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 5

Thr Trp Ala Ser Arg Gln Glu Pro Ser Gln Gly Thr Thr Thr Phe Ala
1               5                   10                  15

Val Thr Ser

<210> SEQ ID NO 6
<211> LENGTH: 104
<212> TYPE: PRT
<213> ORGANISM: Homo sapiens

<400> SEQUENCE: 6

Arg Pro Glu Val His Leu Leu Pro Pro Ser Glu Glu Leu Ala Leu
1               5                   10                  15

Asn Glu Leu Val Thr Leu Thr Cys Leu Ala Arg Gly Phe Ser Pro Lys
                20                  25                  30

Asp Val Leu Val Arg Trp Leu Gln Gly Ser Gln Glu Leu Pro Arg Glu
            35                  40                  45

Lys Tyr Leu Thr Trp Ala Ser Arg Gln Glu Pro Ser Gln Gly Thr Thr
50                  55                  60

Thr Phe Ala Val Thr Ser Ile Leu Arg Val Ala Ala Glu Asp Trp Lys
65                  70                  75                  80

Lys Gly Asp Thr Phe Ser Cys Met Val Gly His Glu Ala Leu Pro Leu
                85                  90                  95

Ala Phe Thr Gln Lys Thr Ile Asp
            100

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Leu Val Pro Arg Gly Ser
1               5

<210> SEQ ID NO 8
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
                20                  25                  30

Gly Ser Gly Val Pro Gly Ser Gly Val Pro Gly Ser Gly Val Pro Gly
            35                  40                  45

Ser Gly Val Pro Gly Ser Gly Val Pro Gly Ser Gly Val Pro Gly Ser
50                  55                  60

Gly Val Pro Gly Ser Gly Val Pro Gly Ser Gly Val Pro Gly Ser Gly
65                  70                  75                  80
```

Val Pro Gly Ser Gly Val Pro Gly Ser Gly Val Pro Gly Ser Gly Val
            85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
            115                 120                 125

Ser Gly Val Pro Gly Ser Gly Val Pro Gly Ser Gly Val Pro Gly Ser
            130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
            165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
            195                 200                 205

Ser Gly Val Pro Gly Ser Gly Val Pro Gly Ser Gly Val Pro Gly Ser
            210                 215                 220

Gly Val Pro Gly Ser Gly Val Pro Gly Ser Gly Val Pro Gly Ser Gly
225                 230                 235                 240

Val Pro Gly Ser Gly Val Pro Gly Ser Gly Val Pro Gly Ser Gly Val
            245                 250                 255

Pro Gly Ser Gly Val Pro Gly Ser Gly Val Pro Gly Ser Gly Val Pro
            260                 265                 270

Gly Ser Gly Val Pro Gly Ser Gly Val Pro Gly Ser Gly Val Pro Gly
            275                 280                 285

Ser Gly Val Pro Gly Ser Gly Val Pro Gly Ser Gly Val Pro Gly Ser
            290                 295                 300

Gly Val Pro Gly Ser Gly Val Pro Gly Ser Gly Val Pro Gly Ser Gly
305                 310                 315                 320

Val Pro Gly Ser Gly Val Pro Gly Ser Gly Val Pro Gly Ser Gly Val
            325                 330                 335

Pro Gly Ser Gly Val Pro Gly Ser Gly Val Pro Gly Ser Gly Val Pro
            340                 345                 350

Gly Ser Gly Val Pro Gly Ser Gly Val Pro Gly Ser Gly Val Pro Gly
            355                 360                 365

Ser Gly Val Pro Gly Ser Gly Val Pro Gly Ser Gly Val Pro Gly Ser
            370                 375                 380

Gly Val Pro Gly Ser Gly Val Pro Gly Ser Gly Val Pro Gly Ser Gly
385                 390                 395                 400

Val Pro Gly Ser Gly Val Pro Gly Ser Gly Val Pro Gly Ser Gly Val
            405                 410                 415

Pro Gly Ser Gly Val Pro Gly Ser Gly Val Pro Gly Ser Gly Val Pro
            420                 425                 430

Gly Ser Gly Val Pro Gly Ser Gly Val Pro Gly Ser Gly Val Pro Gly
            435                 440                 445

Ser Gly Val Pro Gly Ser Gly Val Pro Gly Ser Gly Val Pro Gly Ser
            450                 455                 460

Gly Val Pro Gly Ser Gly Val Pro Gly Ser Gly Val Pro Gly Ser Gly
465                 470                 475                 480

Tyr

<210> SEQ ID NO 9

```
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Pro Gly Ile Gly Val Pro Gly Ile Gly Val Pro Gly Ile Gly Val
1               5                   10                  15

Pro Gly Ile Gly Val Pro Gly Ile Gly Val Pro Gly Ile Gly Val Pro
            20                  25                  30

Gly Ile Gly Val Pro Gly Ile Gly Val Pro Gly Ile Gly Val Pro Gly
        35                  40                  45

Ile Gly Val Pro Gly Ile Gly Val Pro Gly Ile Gly Val Pro Gly Ile
    50                  55                  60

Gly Val Pro Gly Ile Gly Val Pro Gly Ile Gly Val Pro Gly Ile Gly
65                  70                  75                  80

Val Pro Gly Ile Gly Val Pro Gly Ile Gly Val Pro Gly Ile Gly Val
                85                  90                  95

Pro Gly Ile Gly Val Pro Gly Ile Gly Val Pro Gly Ile Gly Val Pro
            100                 105                 110

Gly Ile Gly Val Pro Gly Ile Gly Val Pro Gly Ile Gly Val Pro Gly
        115                 120                 125

Ile Gly Val Pro Gly Ile Gly Val Pro Gly Ile Gly Val Pro Gly Ile
    130                 135                 140

Gly Val Pro Gly Ile Gly Val Pro Gly Ile Gly Val Pro Gly Ile Gly
145                 150                 155                 160

Val Pro Gly Ile Gly Val Pro Gly Ile Gly Val Pro Gly Ile Gly Val
                165                 170                 175

Pro Gly Ile Gly Val Pro Gly Ile Gly Val Pro Gly Ile Gly Val Pro
            180                 185                 190

Gly Ile Gly Val Pro Gly Ile Gly Val Pro Gly Ile Gly Val Pro Gly
        195                 200                 205

Ile Gly Val Pro Gly Ile Gly Val Pro Gly Ile Gly Val Pro Gly Ile
    210                 215                 220

Gly Val Pro Gly Ile Gly Val Pro Gly Ile Gly Val Pro Gly Ile Gly
225                 230                 235                 240

Val Pro Gly Ile Gly Val Pro Gly Ile Gly Val Pro Gly Ile Gly Val
                245                 250                 255

Pro Gly Ile Gly Val Pro Gly Ile Gly Val Pro Gly Ile Gly Val Pro
            260                 265                 270

Gly Ile Gly Val Pro Gly Ile Gly Val Pro Gly Ile Gly Val Pro Gly
        275                 280                 285

Ile Gly Val Pro Gly Ile Gly Val Pro Gly Ile Gly Val Pro Gly Ile
    290                 295                 300

Gly Val Pro Gly Ile Gly Val Pro Gly Ile Gly Val Pro Gly Ile Gly
305                 310                 315                 320

Val Pro Gly Ile Gly Val Pro Gly Ile Gly Val Pro Gly Ile Gly Val
                325                 330                 335

Pro Gly Ile Gly Val Pro Gly Ile Gly Val Pro Gly Ile Gly Val Pro
            340                 345                 350

Gly Ile Gly Val Pro Gly Ile Gly Val Pro Gly Ile Gly Val Pro Gly
        355                 360                 365

Ile Gly Val Pro Gly Ile Gly Val Pro Gly Ile Gly Val Pro Gly Ile
```

```
                 370                 375                 380

Gly Val Pro Gly Ile Gly Val Pro Gly Ile Gly Val Pro Gly Ile Gly
385                 390                 395                 400

Val Pro Gly Ile Gly Val Pro Gly Ile Gly Val Pro Gly Ile Gly Val
                405                 410                 415

Pro Gly Ile Gly Val Pro Gly Ile Gly Val Pro Gly Ile Gly Val Pro
            420                 425                 430

Gly Ile Gly Val Pro Gly Ile Gly Val Pro Gly Ile Gly Val Pro Gly
        435                 440                 445

Ile Gly Val Pro Gly Ile Gly Val Pro Gly Ile Gly Val Pro Gly Ile
    450                 455                 460

Gly Val Pro Gly Ile Gly Val Pro Gly Ile Gly Val Pro Gly Ile Gly
465                 470                 475                 480

Tyr

<210> SEQ ID NO 10
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Pro Gly Ser Gly Val Pro Gly Ser Gly Val Pro Gly Ser Gly
1               5                   10                  15

Val Pro Gly Ser Gly Val Pro Gly Ser Gly Val Pro Gly Ser Gly Val
            20                  25                  30

Pro Gly Ser Gly Val Pro Gly Ser Gly Val Pro Gly Ser Gly Val Pro
        35                  40                  45

Gly Ser Gly Val Pro Gly Ser Gly Val Pro Gly Ser Gly Val Pro Gly
    50                  55                  60

Ser Gly Val Pro Gly Ser Gly Val Pro Gly Ser Gly Val Pro Gly Ser
65                  70                  75                  80

Gly Val Pro Gly Ser Gly Val Pro Gly Ser Gly Val Pro Gly Ser Gly
                85                  90                  95

Val Pro Gly Ser Gly Val Pro Gly Ser Gly Val Pro Gly Ser Gly Val
            100                 105                 110

Pro Gly Ser Gly Val Pro Gly Ser Gly Val Pro Gly Ser Gly Val Pro
        115                 120                 125

Gly Ser Gly Val Pro Gly Ser Gly Val Pro Gly Ser Gly Val Pro Gly
    130                 135                 140

Ser Gly Val Pro Gly Ser Gly Val Pro Gly Ser Gly Val Pro Gly Ser
145                 150                 155                 160

Gly Val Pro Gly Ser Gly Val Pro Gly Ser Gly Val Pro Gly Ser Gly
                165                 170                 175

Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
    210                 215                 220

Ser Gly Val Pro Gly Ser Gly Val Pro Gly Ser Gly Val Pro Gly Ser
225                 230                 235                 240

Gly Val Pro Gly Ile Gly Val Pro Gly Ile Gly Val Pro Gly Ile Gly
```

```
                        245                 250                 255
Val Pro Gly Ile Gly Val Pro Gly Ile Gly Val Pro Gly Ile Gly Val
                260                 265                 270
Pro Gly Ile Gly Val Pro Gly Ile Gly Val Pro Gly Ile Gly Val Pro
            275                 280                 285
Gly Ile Gly Val Pro Gly Ile Gly Val Pro Gly Ile Gly Val Pro Gly
        290                 295                 300
Ile Gly Val Pro Gly Ile Gly Val Pro Gly Ile Gly Val Pro Gly Ile
305                 310                 315                 320
Gly Val Pro Gly Ile Gly Val Pro Gly Ile Gly Val Pro Gly Ile Gly
                325                 330                 335
Val Pro Gly Ile Gly Val Pro Gly Ile Gly Val Pro Gly Ile Gly Val
            340                 345                 350
Pro Gly Ile Gly Val Pro Gly Ile Gly Val Pro Gly Ile Gly Val Pro
        355                 360                 365
Gly Ile Gly Val Pro Gly Ile Gly Val Pro Gly Ile Gly Val Pro Gly
    370                 375                 380
Ile Gly Val Pro Gly Ile Gly Val Pro Gly Ile Gly Val Pro Gly Ile
385                 390                 395                 400
Gly Val Pro Gly Ile Gly Val Pro Gly Ile Gly Val Pro Gly Ile Gly
                405                 410                 415
Val Pro Gly Ile Gly Val Pro Gly Ile Gly Val Pro Gly Ile Gly Val
            420                 425                 430
Pro Gly Ile Gly Val Pro Gly Ile Gly Val Pro Gly Ile Gly Val Pro
        435                 440                 445
Gly Ile Gly Val Pro Gly Ile Gly Val Pro Gly Ile Gly Val Pro Gly
    450                 455                 460
Ile Gly Val Pro Gly Ile Gly Val Pro Gly Ile Gly Val Pro Gly Ile
465                 470                 475                 480
Gly Tyr

<210> SEQ ID NO 11
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ala Ile Thr Val Gly Asn Lys Asn Asn Asp Lys Leu Thr Leu Trp
1               5                   10                  15
Thr Thr Pro Ala Pro Ser Pro Asn Cys Arg Leu Asn Ala Glu Lys Asp
                20                  25                  30
Ala Lys Leu Thr Leu Val Leu Thr Lys Cys Gly Ser Gln Ile Leu Ala
            35                  40                  45
Thr Val Ser Val Leu Ala Val Lys Gly Ser Leu Ala Pro Ile Ser Gly
        50                  55                  60
Thr Val Gln Ser Ala His Leu Ile Ile Arg Phe Asp Glu Asn Gly Val
65                  70                  75                  80
Leu Leu Asn Asn Ser Phe Leu Asp Pro Glu Tyr Trp Asn Phe Arg Asn
                85                  90                  95
Gly Asp Leu Thr Glu Gly Thr Ala Tyr Thr Asn Ala Val Gly Phe Met
                100                 105                 110
Pro Asn Leu Ser Ala Tyr Pro Lys Ser His Gly Lys Thr Ala Lys Ser
```

```
            115                 120                 125
Asn Ile Val Ser Gln Val Tyr Leu Asn Gly Asp Lys Thr Lys Pro Val
    130                 135                 140

Thr Leu Thr Ile Thr Leu Asn Gly Thr Gln Glu Thr Gly Asp Thr Thr
145                 150                 155                 160

Pro Ser Ala Tyr Ser Met Ser Phe Ser Trp Asp Trp Ser Gly His Asn
                165                 170                 175

Tyr Ile Asn Glu Ile Phe Ala Thr Ser Ser Tyr Thr Phe Ser Tyr Ile
            180                 185                 190

Ala Gln Glu Gly Leu Val Pro Arg Gly Ser Gly
        195                 200

<210> SEQ ID NO 12
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
            20                  25                  30

Gly Ser Gly Val Pro Gly Ser Gly Val Pro Gly Ser Gly Val Pro Gly
        35                  40                  45

Ser Gly Val Pro Gly Ser Gly Val Pro Gly Ser Gly Val Pro Gly Ser
    50                  55                  60

Gly Val Pro Gly Ser Gly Val Pro Gly Ser Gly Val Pro Gly Ser Gly
65                  70                  75                  80

Val Pro Gly Ser Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125

Ser Gly Val Pro Gly Ser Gly Val Pro Gly Ser Gly Val Pro Gly Ser
    130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
                165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
        195                 200                 205

Ser Gly Val Pro Gly Ser Gly Val Pro Gly Ser Gly Val Pro Gly Ser
    210                 215                 220

Gly Val Pro Gly Ser Gly Val Pro Gly Ser Gly Val Pro Gly Ser Gly
225                 230                 235                 240

Val Pro Gly Ile Gly Val Pro Gly Ile Gly Val Pro Gly Ile Gly Val
                245                 250                 255

Pro Gly Ile Gly Val Pro Gly Ile Gly Val Pro Gly Ile Gly Val Pro
            260                 265                 270
```

```
Gly Ile Gly Val Pro Gly Ile Gly Val Pro Gly Ile Gly Val Pro Gly
            275                 280                 285
Ile Gly Val Pro Gly Ile Gly Val Pro Gly Ile Gly Val Pro Gly Ile
            290                 295                 300
Gly Val Pro Gly Ile Gly Val Pro Gly Ile Gly Val Pro Gly Ile Gly
305                 310                 315                 320
Val Pro Gly Ile Gly Val Pro Gly Ile Gly Val Pro Gly Ile Gly Val
            325                 330                 335
Pro Gly Ile Gly Val Pro Gly Ile Gly Val Pro Gly Ile Gly Val Pro
            340                 345                 350
Gly Ile Gly Val Pro Gly Ile Gly Val Pro Gly Ile Gly Val Pro Gly
            355                 360                 365
Ile Gly Val Pro Gly Ile Gly Val Pro Gly Ile Gly Val Pro Gly Ile
            370                 375                 380
Gly Val Pro Gly Ile Gly Val Pro Gly Ile Gly Val Pro Gly Ile Gly
385                 390                 395                 400
Val Pro Gly Ile Gly Val Pro Gly Ile Gly Val Pro Gly Ile Gly Val
            405                 410                 415
Pro Gly Ile Gly Val Pro Gly Ile Gly Val Pro Gly Ile Gly Val Pro
            420                 425                 430
Gly Ile Gly Val Pro Gly Ile Gly Val Pro Gly Ile Gly Val Pro Gly
            435                 440                 445
Ile Gly Val Pro Gly Ile Gly Val Pro Gly Ile Gly Val Pro Gly Ile
            450                 455                 460
Gly Val Pro Gly Ile Gly Val Pro Gly Ile Gly Val Pro Gly Ile Gly
465                 470                 475                 480

<210> SEQ ID NO 13
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Pro Gly Ser Gly Val Pro Gly Ser Gly Val Pro Gly Ser Gly Val
1               5                   10                  15
Pro Gly Ser Gly Val Pro Gly Ser Gly Val Pro Gly Ser Gly Val Pro
            20                  25                  30
Gly Ser Gly Val Pro Gly Ser Gly Val Pro Gly Ser Gly Val Pro Gly
            35                  40                  45
Ser Gly Val Pro Gly Ser Gly Val Pro Gly Ser Gly Val Pro Gly Ser
            50                  55                  60
Gly Val Pro Gly Ser Gly Val Pro Gly Ser Gly Val Pro Gly Ser Gly
65                  70                  75                  80
Val Pro Gly Ser Gly Val Pro Gly Ser Gly Val Pro Gly Ser Gly Val
            85                  90                  95
Pro Gly Ser Gly Val Pro Gly Ser Gly Val Pro Gly Ser Gly Val Pro
            100                 105                 110
Gly Ser Gly Val Pro Gly Ser Gly Val Pro Gly Ser Gly Val Pro Gly
            115                 120                 125
Ser Gly Val Pro Gly Ser Gly Val Pro Gly Ser Gly Val Pro Gly Ser
            130                 135                 140
Gly Val Pro Gly Ser Gly Val Pro Gly Ser Gly Val Pro Gly Ser Gly
145                 150                 155                 160
```

```
Val Pro Gly Ser Gly Val Pro Gly Ser Gly Val Pro Gly Ser Gly Val
            165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
            195                 200                 205

Ser Gly Val Pro Gly Ser Gly Val Pro Gly Ser Gly Val Pro Gly Ser
            210                 215                 220

Gly Val Pro Gly Ser Gly Val Pro Gly Ser Gly Val Pro Gly Ser Gly
225                 230                 235                 240

Val Pro Gly Ser Gly Val Pro Gly Ser Gly Val Pro Gly Ser Gly Val
            245                 250                 255

Pro Gly Ser Gly Val Pro Gly Ser Gly Val Pro Gly Ser Gly Val Pro
            260                 265                 270

Gly Ser Gly Val Pro Gly Ser Gly Val Pro Gly Ser Gly Val Pro Gly
            275                 280                 285

Ser Gly Val Pro Gly Ser Gly Val Pro Gly Ser Gly Val Pro Gly Ser
            290                 295                 300

Gly Val Pro Gly Ser Gly Val Pro Gly Ser Gly Val Pro Gly Ser Gly
305                 310                 315                 320

Val Pro Gly Ser Gly Val Pro Gly Ser Gly Val Pro Gly Ser Gly Val
            325                 330                 335

Pro Gly Ser Gly Val Pro Gly Ser Gly Val Pro Gly Ser Gly Val Pro
            340                 345                 350

Gly Ser Gly Val Pro Gly Ser Gly Val Pro Gly Ser Gly Val Pro Gly
            355                 360                 365

Ser Gly Val Pro Gly Ser Gly Val Pro Gly Ser Gly Val Pro Gly Ser
            370                 375                 380

Gly Val Pro Gly Ser Gly Val Pro Gly Ser Gly Val Pro Gly Ser Gly
385                 390                 395                 400

Val Pro Gly Ser Gly Val Pro Gly Ser Gly Val Pro Gly Ser Gly Val
            405                 410                 415

Pro Gly Ser Gly Val Pro Gly Ser Gly Val Pro Gly Ser Gly Val Pro
            420                 425                 430

Gly Ser Gly Val Pro Gly Ser Gly Val Pro Gly Ser Gly Val Pro Gly
            435                 440                 445

Ser Gly Val Pro Gly Ser Gly Val Pro Gly Ser Gly Val Pro Gly Ser
            450                 455                 460

Gly Val Pro Gly Ser Gly Val Pro Gly Ser Gly Val Pro Gly Ser Gly
465                 470                 475                 480

<210> SEQ ID NO 14
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Val Pro Gly Ile Gly Val Pro Gly Ile Gly Val Pro Gly Ile Gly Val
1               5                   10                  15

Pro Gly Ile Gly Val Pro Gly Ile Gly Val Pro Gly Ile Gly Val Pro
            20                  25                  30

Gly Ile Gly Val Pro Gly Ile Gly Val Pro Gly Ile Gly Val Pro Gly
```

```
                35                  40                  45
Ile Gly Val Pro Gly Ile Gly Val Pro Gly Ile Gly Val Pro Gly Ile
 50                  55                  60
Gly Val Pro Gly Ile Gly Val Pro Gly Ile Gly Val Pro Gly Ile Gly
 65                  70                  75                  80
Val Pro Gly Ile Gly Val Pro Gly Ile Gly Val Pro Gly Ile Gly Val
                85                  90                  95
Pro Gly Ile Gly Val Pro Gly Ile Gly Val Pro Gly Ile Gly Val Pro
            100                 105                 110
Gly Ile Gly Val Pro Gly Ile Gly Val Pro Gly Ile Gly Val Pro Gly
            115                 120                 125
Ile Gly Val Pro Gly Ile Gly Val Pro Gly Ile Gly Val Pro Gly Ile
            130                 135                 140
Gly Val Pro Gly Ile Gly Val Pro Gly Ile Gly Val Pro Gly Ile Gly
145                 150                 155                 160
Val Pro Gly Ile Gly Val Pro Gly Ile Gly Val Pro Gly Ile Gly Val
                165                 170                 175
Pro Gly Ile Gly Val Pro Gly Ile Gly Val Pro Gly Ile Gly Val Pro
            180                 185                 190
Gly Ile Gly Val Pro Gly Ile Gly Val Pro Gly Ile Gly Val Pro Gly
            195                 200                 205
Ile Gly Val Pro Gly Ile Gly Val Pro Gly Ile Gly Val Pro Gly Ile
            210                 215                 220
Gly Val Pro Gly Ile Gly Val Pro Gly Ile Gly Val Pro Gly Ile Gly
225                 230                 235                 240
Val Pro Gly Ile Gly Val Pro Gly Ile Gly Val Pro Gly Ile Gly Val
                245                 250                 255
Pro Gly Ile Gly Val Pro Gly Ile Gly Val Pro Gly Ile Gly Val Pro
            260                 265                 270
Gly Ile Gly Val Pro Gly Ile Gly Val Pro Gly Ile Gly Val Pro Gly
            275                 280                 285
Ile Gly Val Pro Gly Ile Gly Val Pro Gly Ile Gly Val Pro Gly Ile
            290                 295                 300
Gly Val Pro Gly Ile Gly Val Pro Gly Ile Gly Val Pro Gly Ile Gly
305                 310                 315                 320
Val Pro Gly Ile Gly Val Pro Gly Ile Gly Val Pro Gly Ile Gly Val
                325                 330                 335
Pro Gly Ile Gly Val Pro Gly Ile Gly Val Pro Gly Ile Gly Val Pro
            340                 345                 350
Gly Ile Gly Val Pro Gly Ile Gly Val Pro Gly Ile Gly Val Pro Gly
            355                 360                 365
Ile Gly Val Pro Gly Ile Gly Val Pro Gly Ile Gly Val Pro Gly Ile
            370                 375                 380
Gly Val Pro Gly Ile Gly Val Pro Gly Ile Gly Val Pro Gly Ile Gly
385                 390                 395                 400
Val Pro Gly Ile Gly Val Pro Gly Ile Gly Val Pro Gly Ile Gly Val
                405                 410                 415
Pro Gly Ile Gly Val Pro Gly Ile Gly Val Pro Gly Ile Gly Val Pro
            420                 425                 430
Gly Ile Gly Val Pro Gly Ile Gly Val Pro Gly Ile Gly Val Pro Gly
            435                 440                 445
```

```
Ile Gly Val Pro Gly Ile Gly Val Pro Gly Ile Gly Val Pro Gly Ile
    450                 455                 460

Gly Val Pro Gly Ile Gly Val Pro Gly Ile Gly Val Pro Gly Ile Gly
465                 470                 475                 480
```